(12) United States Patent
Ye et al.

(10) Patent No.: US 9,624,254 B2
(45) Date of Patent: *Apr. 18, 2017

(54) HYDROXYSAFFLOR YELLOW PHARMACEUTICAL SALTS

(71) Applicant: ZHEJIANG YONGNING PHARMACEUTICAL CO LTD, Taizhou, Zhejiang (CN)

(72) Inventors: Fengqi Ye, Zhejiang (CN); Ben Cai, Zhejiang (CN); Min Lu, Zhejiang (CN); Yongling Chen, Zhejiang (CN)

(73) Assignee: ZHEJIANG YONGNING PHARMACEUTICAL CO., LTD, Taizhou, Zhejiang, Chian ( * ) Notice: Subject to any disclaimer, the term of this patent is extended or adjusted under 35 U.S.C. 154(b) by 93 days.

This patent is subject to a terminal disclaimer.

(21) Appl. No.: 14/417,811

(22) PCT Filed: Feb. 26, 2014

(86) PCT No.: PCT/CN2014/000180
§ 371 (c)(1),
(2) Date: Jan. 28, 2015

(87) PCT Pub. No.: WO2014/121666
PCT Pub. Date: Aug. 14, 2014

(65) Prior Publication Data
US 2015/0197537 A1  Jul. 16, 2015

(30) Foreign Application Priority Data

Feb. 7, 2013 (CN) .......................... 2013 1 0048480
Jun. 8, 2013 (CN) .......................... 2013 1 0231483

(51) Int. Cl.
*C07H 7/04* (2006.01)
*C07H 15/203* (2006.01)
*A61K 36/286* (2006.01)
*C07D 309/10* (2006.01)

(52) U.S. Cl.
CPC ......... *C07H 15/203* (2013.01); *A61K 36/286* (2013.01); *C07D 309/10* (2013.01)

(58) Field of Classification Search
None
See application file for complete search history.

(56) References Cited

U.S. PATENT DOCUMENTS 9,243,019 B2 * 1/2016 Ye .................... C07D 309/04

* cited by examiner

*Primary Examiner* — Traviss C McIntosh, III

(57) ABSTRACT

A new pharmaceutically acceptable salt of hydroxysafflor yellow A as presented in formula (I), in particular new monomer compounds of potassium, ammonium, calcium, and magnesium salts of hydroxysafflor yellow A, preparation method therefor, and medical uses thereof are provided. Compared to hydroxysafflor yellow A, the hydroxysafflor yellow A pharmaceutical salts of the present invention have a purity of at least 98% and are monomer compounds that are safer, more effective, stable, and controllable. The salts have the effects against PAF- or ADP-induced platelet aggregation, and can be used in treating blood circulatory disorders such as platelet aggregation, coronary artery diseases, angina, and acute cerebral ischemia to the effect comparable to hydroxysafflor yellow A, Formula (I)

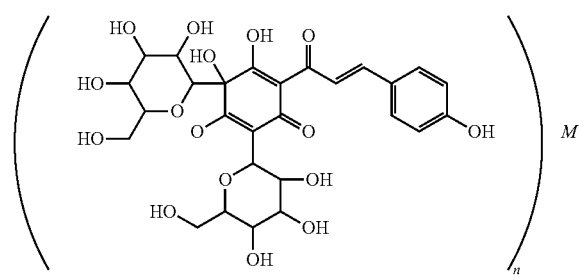

wherein, n and M are defined as in the description.

8 Claims, 4 Drawing Sheets

HYDROXYSAFFLOR YELLOW PHARMACEUTICAL SALTS

CROSS REFERENCE OF RELATED APPLICATION

This is a U.S. National Stage under 35 U.S.C 371 of the International Application PCT/CN2014/000180, filed Feb. 26, 2014, which claims priority under 35 U.S.C. 119(a-d) to CN 201310048480.4, filed Feb. 7, 2013; and CN 201310231483.1, filed Jun. 8, 2013.

BACKGROUND OF THE PRESENT INVENTION

Field of Invention

The present invention provides new hydroxysafflor yellow pharmaceutical salts, in particular new pharmaceutically acceptable salt of hydroxysafflor yellow A, preparation method thereof, lyophilized powder for injection and medical uses thereof. It relates to the field of pharmaceutical chemistry.

Description of Related Arts

Chinese medicine safflower is dried flower of *Carthamus tinctouius* L., which is a common Chinese medicine for activating blood and dissipating blood stasis, and is applicable for treating blood circulation disorders such as coronary heart disease and angina pectoris. Hydroxysafflor yellow A is a compound with a mono-chalcone glycoside structure, and is a water-soluble portion of the safflower with the most effective pharmacological effect, which can inhibit platelet aggregation and release induced by platelet activating factors, and competitively inhibit combination of the platelet activating factor and the platelet receptor. Therefore, the hydroxysafflor yellow A is an effective ingredient of the safflor yellow for activating blood and dissipating blood stasis. According to research results, the hydroxysafflor yellow A has many pharmacological effects on cardiovascular such as anticoagulant, promoting fibrinolysis, anti-thrombosis, and improving microcirculation.

As the component with the highest content in hydroxysafflor yellow, hydroxysafflor yellow A has been demonstrated pharmaceutically valuable in the treatment of cardiovascular diseases. This mechanism of action is also well known. A number of manufacturing processes of hydroxysafflor yellow A have already been disclosed in present technology, including steps such as using safflower as the raw material, extraction with water, macroporous adsorptive resin separation, dextran gel chromatography, and ultrafiltration, so as to yield hydroxysafflor yellow A for injection. However, hydroxysafflor yellow A prepared by present manufacturing process does not have adequate purity, and generally contains over 10% of impurities. And structure and property of such impurities have not been characterized yet. Therefore, there is certain uncontrollability in terms of quality, and the product may be influenced, in particular stability and safety of medicine for injection. CN102675379A disclosed a method for extracting and refining hydroxysafflor yellow A from safflower, in particular five steps including extraction from traditional Chinese medicine safflower, purifying through weak-base ion exchange resin, purifying through neutral polarity macroporous adsorptive resin, purifying through non-polar macroporous adsorptive resin, and lyophilization, which only yields over 80% of hydroxysafflor yellow A.

SUMMARY OF THE PRESENT INVENTION

To overcome conventional technology flaw, the present invention provides a new composition of pharmaceutically acceptable salt of hydroxysafflor yellow A. Its purity is guaranteed to be over 98%, and number of impurities is controlled to less than 5. It will become a new monomer compound which is superior as compared to hydroxysafflor yellow A with regard to safety, efficacy, stability and controllability when used to treat various blood circulation disorders such as coronary heart disease, angina, stroke, etc.

Technical solutions of the present invention are as following:

One of the objectives of the present invention is to provide a pharmaceutically acceptable salt of hydroxysafflor yellow A as presented in a formula (I):

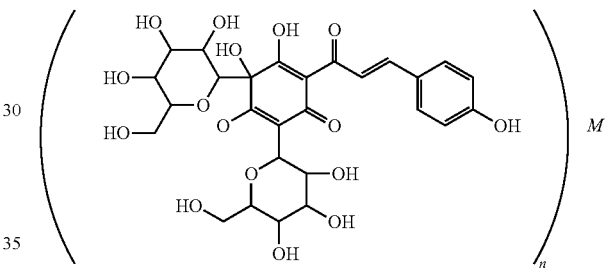

Formula (I)

wherein n is 1 or 2, and M is chosen from Ca, Mg, K, NH4 or

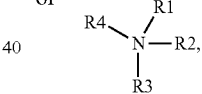

wherein R1, R2, R3 and R4 may be identical or different, and chosen from a hydrogen or an alkyl group independently.

Preferably, the pharmaceutically acceptable salt of hydroxysafflor yellow A described above is chosen from a potassium salt of a formula (II), an ammonium salt of a formula (III), a calcium salt of a formula (IV), or a magnesium salt of a formula (V):

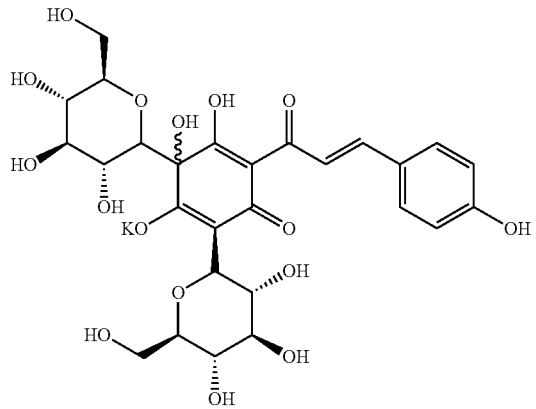

Formula (II)

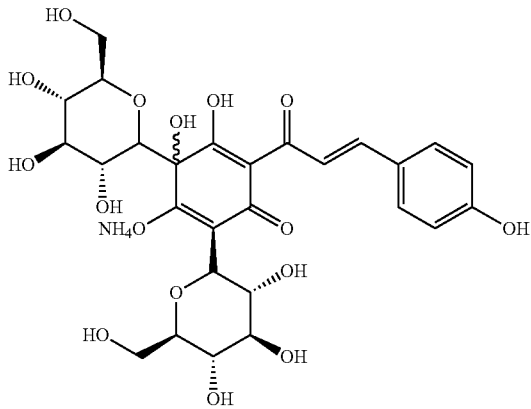

Formula (III)

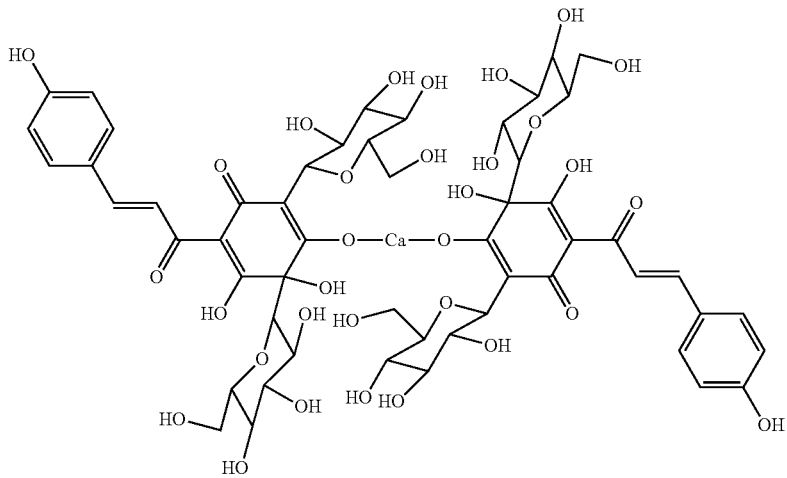

Formula (IV)

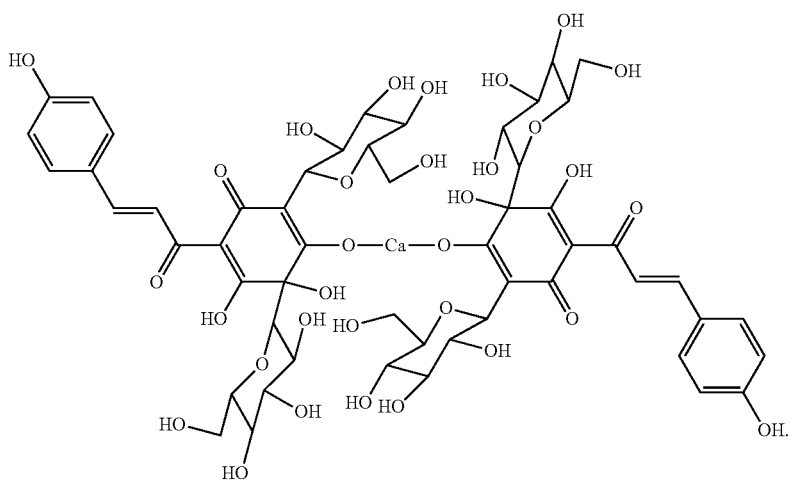

Formula (V)

As another objective of the present invention, a method to prepare pharmaceutically acceptable salt of hydroxysafflor yellow A described above, including steps of extracting from saffron herbs, converting with strongly acidic H-type cation exchange resin, macroporous adsorptive resin separating, processing with dextran gel chromatographic separation, and ultrafiltrating, is also provided, characterized by:

(1) extracting from saffron herbs: using saffron herbs as a raw material, wherein an extract containing hydroxysafflor yellow A is obtained through water extraction;

(2) converting with strongly acidic H-type cation exchange resin: passing the extract obtained in the Step (1) through a strongly acidic H-type cation exchange resin column, collecting eluent, adding potassium hydroxide, ammonium hydroxide, alkylamine or alkyl ammonium, magnesium hydroxide, calcium hydroxide, magnesium carbonate or calcium carbonate, to convert the hydroxysafflor yellow A into the pharmaceutically acceptable salt of the hydroxysafflor yellow A, and then collecting eluent containing the pharmaceutically acceptable salt of the hydroxysafflor yellow A;

(3) macroporous adsorptive resin separating: separating the eluent containing the pharmaceutically acceptable salt of the hydroxysafflor yellow A prepared in the Step (2) with a macroporous adsorptive resin column, using water as eluent; collecting the eluent and concentrating under a reduced pressure, to yield a crude pharmaceutically acceptable salt of the hydroxysafflor yellow A;

(4) processing with dextran gel chromatography: undergoing the crude pharmaceutically acceptable salt of the hydroxysafflor yellow A obtained in the Step (3) with dextran gel chromatographic separation, using water as eluent, collecting the eluent containing the pharmaceutically acceptable salt of the hydroxysafflor yellow A; and (5) ultrafiltrating: concentrating the eluent containing the pharmaceutically acceptable salt of the hydroxysafflor yellow A obtained from the Step (4), and then filtering or centrifuging; ultrafiltrating by using an ultrafiltration membrane with molecular weight cutoff (MWCO) of 8000-10000 Daltons to obtain ultrafiltrate, which is subsequently dried to yield the pharmaceutically acceptable salt of the hydroxysafflor yellow A.

Preferably, wherein the cation exchange resin described in the Step (2) is the strongly acidic H-type cation exchange resin, which is chosen from 001*7 ion exchange resin or macroporous HB-8 exchange resin.

Strongly acidic H-type cation exchange resin used in the present invention may be commercially available strongly acidic H-type cation exchange resin, such as 001*7 ion exchange resin, or macroporous HB-8 exchange resin. Both of them could be purchased from Shanghai Huazhen Sci. & Tech. Co., Ltd, and may be regenerated with HCl and reused.

As another objective of the present invention, a method to prepare pharmaceutically acceptable salt of hydroxysafflor yellow A described above, including steps of extracting from saffron herbs, macroporous adsorptive resin separating, processing with dextran gel chromatography, ultrafiltrating, acidifying and salifying, characterized by:

(1) extracting from saffron herbs: using saffron herbs as a raw material, wherein an extract containing hydroxysafflor yellow A is obtained through water extraction;

(2) macroporous adsorptive resin separating: separating the extract containing the hydroxysafflor yellow prepared in the Step (1) with a macroporous adsorptive resin column, using water as eluent; Collecting the eluent and concentrating under a reduced pressure, to yield a crude hydroxysafflor yellow;

(3) processing with dextran gel chromatography: undergoing the crude hydroxysafflor yellow prepared in the Step (2) with dextran gel chromatographic separation, using water as eluent; collecting the eluent containing the hydroxysafflor yellow;

(4) ultrafiltrating: concentrating the eluent containing the hydroxysafflor yellow A obtained from the Step (3), and then filtering or centrifuging; ultrafiltrating by using an ultrafiltration membrane with MWCO of 8000-10000 Daltons to obtain ultrafiltrate, which is subsequently dried to yield the hydroxysafflor yellow powder;

(5) acidifying: adding water and then acid into the hydroxysafflor yellow powder obtained from the Step (4); allowing to stand for 2-24 hours in a cool place, until an amber solid of hydroxysafflor yellow A is formed; then removing the supernatant liquid through filtering; and (6) salifying: adding water, and then potassium hydroxide, ammonium hydroxide, alkylamine or alkyl ammonium, magnesium hydroxide, calcium hydroxide, magnesium carbonate or calcium carbonate, into the hydroxysafflor yellow A obtained in the Step (5) to convert the hydroxysafflor yellow A into the pharmaceutically acceptable salt of the hydroxysafflor yellow A; wherein again ultrafiltration is carried out with an ultrafiltration membrane; and the pharmaceutically acceptable salt of the hydroxysafflor yellow A is obtained through lyophilisation.

As another objective of the present invention, a pharmaceutical composition, comprising therapeutic amount of pharmaceutically acceptable salt of hydroxysafflor yellow A described above as an active ingredient, and pharmaceutically acceptable carrier as an adjuvant, is also provided.

Pharmaceutically acceptable salt of hydroxysafflor yellow A may be prepared into appropriate formulation for use, such as lyophilized powder for injection or infusion. It may be prepared into: (1) Pharmaceutically acceptable salt of hydroxysafflor yellow A lyophilized powder for injection, 50 mg-200 mg per vial, without adjuvant, or adding mannitol per ratio of 1:0.5-1.5; (2) Pharmaceutically acceptable salt of hydroxysafflor yellow A in sodium chloride solution for injection, with 50 mg-200 mg of pharmaceutically acceptable salt of hydroxysafflor yellow A per each 100 ml of sodium chloride solution for injection; (3) Pharmaceutically acceptable salt of hydroxysafflor yellow A in glucose solution for injection, with 50 mg-200 mg of pharmaceutically acceptable salt of hydroxysafflor yellow A per each 100 ml of glucose solution for injection.

The pharmaceutical composition described above is preferably lyophilized powder for injection, and prepared through a process including the following steps of:

(1) using saffron herbs as a raw material, adding water at 50-100° C. for extraction, which is carried out by extracting with water for 2-3 times, 0.5-24 hours each time; wherein an amount of the water used for extraction is 10-30 times of crude safflower; after extraction, gruffs is filtered out; the extract is cooled to 5-30° C. and allowed to stand for 2-24 hours;

(2) flowing the extract prepared in the Step (1) through strongly acidic H-type cation exchange resin at a rate of 1-30 ml/min; adding potassium hydroxide, ammonium hydroxide, alkylamine or alkyl ammonium, magnesium hydroxide, calcium hydroxide, magnesium carbonate or calcium carbonate, to convert the hydroxysafflor yellow A into the pharmaceutically acceptable salt of the hydroxysafflor yellow A; collecting eluent containing the pharmaceutically acceptable salt of the hydroxysafflor yellow A;

(3) undergoing the eluent prepared in the Step (2) with macroporous adsorptive resin column separation, using purified water as eluent and at an elution flow rate of 10-30 ml/min; collecting the eluent, and concentrating at a reduced pressure, to yield a concentrated solution of a crude pharmaceutically acceptable salt of the hydroxysafflor yellow A;

(4) after filtering or centrifuging the concentrated solution of the crude pharmaceutically acceptable salt of the hydroxysafflor yellow A obtained in the Step (3), providing dextran gel chromatographic separation, using purified water as eluent, and at a controlled linear elution flow rate of 1-10 cm/h; collecting the eluent containing the pharmaceutically acceptable salt of the hydroxysafflor yellow A, and concentrating at the reduced pressure, to yield a concentrated solution;

(5) after filtering or centrifuging the concentrated solution obtained from the Step (4), ultrafiltrating with an ultrafiltration membrane of MWCO 8000-10000 Daltons, to yield ultrafiltrate;

(6) lyophilizing the ultrafiltrate obtained from the Step (5) to yield a refined product of the pharmaceutically acceptable salt of the hydroxysafflor yellow A; and (7) dissolving the refined product of the pharmaceutically acceptable salt of the hydroxysafflor yellow A obtained from the Step (6) in water for injection; wherein resulting solution is filtered through a micropore film of 0.22 μm or the ultrafiltration membrane of MWCO 8000-10000 Daltons, and then transferred into bottles as aliquots; the resulting solution is subsequently lyophilized to yield lyophilized powder for injection of the pharmaceutically acceptable salt of the hydroxysafflor yellow A;

Preferably, the cation exchange resin described above is 001*7 ion exchange resin or macroporous HB-8 exchange resin; the macroporous adsorptive resin is macroporous adsorptive resin HZ801; and the dextran gel chromatography is dextran gel LH-20.

For the method described above in the present invention, adding the medicinal base to convert the hydroxysafflor yellow A into the pharmaceutically acceptable salt of the hydroxysafflor yellow A, wherein an amount of a base added is preferably 0.5-1 time of a molar weight of the hydroxysafflor yellow A.

As one embodiment of the present invention, a potassium hydroxysafflor yellow A of formula (II) and preparation of lyophilized powder for injection thereof, including steps of extracting from saffron herbs, converting with strongly acidic H-type cation exchange resin, macroporous resin separating, processing with dextran gel chromatography and ultrafiltrating, are provided, characterized by: (1) using saffron herbs as the a raw material, wherein an appropriate amount of water at 50-100° C. is added for extraction, which is carried out by extracting with water for 2-3 times, 0.5-24 hours each time. Amount of water used for extraction is 10-30 times of crude safflower. After extraction, the gruffs is filtered out. The extract is cooled to 5-30° C. and allowed to stand for 2-24 hours; (2) the extract is made to flow through strongly acidic H-type cation exchange resin at a rate of 1-30 ml/min Collect the eluent, add the same moles of potassium hydroxide as calculated as hydroxysafflor yellow A, to obtain an eluent containing potassium hydroxysafflor yellow A; (3) macroporous adsorptive resin separation: the eluent obtained in Step (2) undergoes macroporous adsorptive resin HZ801 column separation. The ratio of inner diameter of macroporous adsorptive resin column to column height is 1:8-15. Purified water is used as the eluent, and the elution flow rate is 10-30 ml/min Collect the eluent, and concentrate at reduced pressure, to yield a concentrated solution of crude potassium hydroxysafflor yellow A; (4) dextran gel chromatographic separation: the concentrated solution of crude potassium hydroxysafflor yellow A obtained in Step (3) is filtered or centrifuged, and then undergoes Sephadex LH-20 dextran gel chromatographic separation, with a ratio of diameter to height of chromatographic column being 1:5-20, using purified water as the eluent, and at a controlled linear elution flow rate of 1-10 cm/h. Collect the eluent containing potassium hydroxysafflor yellow A, and concentrate at reduced pressure, to yield a concentrated solution; (5) ultrafiltration: after filtering or centrifuging the concentrated solution obtained from Step (4), ultrafiltration is carried out with an ultrafiltration membrane of MWCO 8000-10000 Daltons, to yield ultrafiltrate; and (6) lyophilization: the ultrafiltrate obtained from Step (5) is lyophilized to yield potassium hydroxysafflor yellow A; if necessary, the refined product of potassium hydroxysafflor yellow A obtained from Step (6) is dissolved in water for injection. The resulting solution is filtered through a micropore film of 0.22 μm or an ultrafiltration membrane of MWCO 8000-10000 Daltons, and then transferred into bottles as aliquots. It is subsequently lyophilized to yield lyophilized powder for injection of potassium hydroxysafflor yellow A.

As another embodiment of the present invention, an ammonium hydroxysafflor yellow A of formula (III) and preparation of lyophilized powder for injection thereof, including steps of extracting from saffron herbs, converting with strongly acidic cation exchange resin, macroporous resin separating, processing with dextran gel chromatographic separation and ultrafiltrating, are provided, characterized by:

(1) using saffron herbs as the raw material, appropriate amount of water at 50-100° C. is added for extraction, which is carried out by extracting with water for 2-3 times, 0.5-24 hours each time. Amount of water used for extraction is 10-30 times of crude safflower. After extraction, the gruffs is filtered out. The extract is cooled to 5-30° C. and allowed to stand for 2-24 hours; (2) the extract is made to flow through strongly acidic cation exchange resin at a rate of 1-30 ml/min Collect the extract, add the same moles of ammonium hydroxide (i.e. ammonia) as calculated as hydroxysafflor yellow A, to obtain an eluent containing ammonium hydroxysafflor yellow A; (3) macroporous adsorptive resin separation: the eluent obtained in Step (2) undergoes macroporous adsorptive resin HZ801 column separation. The ratio of inner diameter of macroporous adsorptive resin column to column height is 1:8-15. Purified water is used as the eluent, and the elution flow rate is 10-30 ml/min Collect the eluent, and concentrate at reduced pressure, to yield a concentrated solution of crude ammonium hydroxysafflor yellow A; (4) dextran gel chromatographic separation: the concentrated solution of crude ammonium hydroxysafflor yellow A obtained in Step (3) is filtered or centrifuged, and then undergoes Sephadex LH-20 dextran gel chromatographic separation, with a ratio of diameter to height of chromatographic column being 1:5-20, using purified water as the eluent, and at a controlled linear elution flow rate of 1-10 cm/h. Collect the eluent containing ammonium hydroxysafflor yellow A, and concentrate at reduced pressure, to yield a concentrated solution; (5) ultrafiltration: after filtering or centrifuging the concentrated solution obtained from Step (4), ultrafiltration is carried out with an ultrafiltration membrane of MWCO 8000-10000 Daltons, to yield ultrafiltrate; and (6) lyophilization: the ultrafiltrate obtained from Step (5) is lyophilized to yield ammonium hydroxysafflor yellow A. If necessary, the refined product of ammonium hydroxysafflor yellow A obtained from Step (6) is dissolved in water for injection. The resulting solution is filtered through a micropore film of 0.22 μm or an ultrafiltration membrane of MWCO 8000-10000 Daltons, and then transferred into bottles as aliquots. It is subsequently lyophilized to yield lyophilized powder for injection of ammonium hydroxysafflor yellow A.

As another embodiment of the present invention, a calcium hydroxysafflor yellow A of formula (IV) and preparation of lyophilized powder for injection thereof, including steps of extracting from saffron herbs, converting with strongly acidic H-type cation exchange resin, macroporous resin separating, dextran gel chromatographic separating and ultrafiltration, are provided, characterized by: (1) using saffron herbs as the raw material, appropriate amount of water at 50-100° C. is added for extraction, which is carried out by extracting with water for 2-3 times, 0.5-24 hours each time. Amount of water used for extraction is 10-30 times of crude safflower. After extraction, the gruffs is filtered out. The extract is cooled to 5-30° C. and allowed to stand for 2-24 hours; (2) the extract is made to flow through strongly acidic H-type cation exchange resin at a rate of 1-30 ml/min. Collect the eluent, add half the moles of $Ca(OH)_2$ as calculated as hydroxysafflor yellow A, to obtain an eluent containing calcium hydroxysafflor yellow A; (3) macroporous adsorptive resin separation: the eluent obtained in Step (2) undergoes macroporous adsorptive resin HZ801 column separation. The ratio of inner diameter of macroporous adsorptive resin column to column height is 1:8-15. Purified water is used as the eluent, and the elution flow rate is 10-30 ml/min Collect the eluent, and concentrate at reduced pressure, to yield a concentrated solution of crude calcium hydroxysafflor yellow A; (4) dextran gel chromatographic separation: the concentrated solution of crude calcium hydroxysafflor yellow A obtained in Step (3) is filtered or centrifuged, and then undergoes Sephadex LH-20 dextran gel chromatographic separation, with a ratio of diameter to height of chromatographic column being 1:5-20, using purified water as the eluent, and at a controlled linear elution flow rate of 1-10 cm/h. Collect the eluent containing calcium hydroxysafflor yellow A, and concentrate at reduced pressure, to yield a concentrated solution; (5) ultrafiltration: after filtering or centrifuging the concentrated solution obtained from Step (4), ultrafiltration is carried out with an ultrafiltration membrane of MWCO 8000-10000 Daltons, to yield ultrafiltrate; and (6) lyophilization: the ultrafiltrate obtained from Step (5) is lyophilized to yield calcium hydroxysafflor yellow A; if necessary, the refined product of calcium hydroxysafflor yellow A obtained from Step (6) is dissolved in water for injection. The resulting solution is filtered through a micropore film of 0.22 μm or an ultrafiltration membrane of MWCO 8000-10000 Daltons, and then transferred into bottles as aliquots. It is subsequently lyophilized to yield lyophilized powder for injection of calcium hydroxysafflor yellow A.

As another embodiment of the present invention, a magnesium hydroxysafflor yellow A of formula (V) and preparation of lyophilized powder for injection thereof, including steps of extracting from saffron herbs, converting with strongly acidic cation exchange resin, macroporous resin separating, dextran gel chromatographic separating and ultrafiltrating, are provided, characterized by: (1) using saffron herbs as the raw material, appropriate amount of water at 50-100° C. is added for extraction, which is carried out by extracting with water for 2-3 times, 0.5-24 hours each time. Amount of water used for extraction is 10-30 times of crude safflower. After extraction, the gruffs is filtered out. The extract is cooled to 5-30° C. and allowed to stand for 2-24 hours; (2) the extract is made to flow through strongly acidic cation exchange resin at a rate of 1-30 ml/min Collect the extract, add half the moles of magnesium hydroxide as calculated as hydroxysafflor yellow A, to obtain an eluent containing magnesium hydroxysafflor yellow A; (3) macroporous adsorptive resin separation: the eluent obtained in Step (2) undergoes macroporous adsorptive resin HZ801 column separation. The ratio of inner diameter of macroporous adsorptive resin column to column height is 1:8-15. Purified water is used as the eluent, and the elution flow rate is 10-30 ml/min Collect the eluent, and concentrate at reduced pressure, to yield a concentrated solution of crude magnesium hydroxysafflor yellow A; (4) dextran gel chromatographic separation: the concentrated solution of crude magnesium hydroxysafflor yellow A obtained in Step (3) is filtered or centrifuged, and then undergoes Sephadex LH-20 dextran gel chromatographic separation, with a ratio of diameter to height of chromatographic column being 1:5-20, using purified water as the eluent, and at a controlled linear elution flow rate of 1-10 cm/h. Collect the eluent containing magnesium hydroxysafflor yellow A, and concentrate at reduced pressure, to yield a concentrated solution; (5) ultrafiltration: after filtering or centrifuging the concentrated solution obtained from Step (4), ultrafiltration is carried out with an ultrafiltration membrane of MWCO 8000-10000 Daltons, to yield ultrafiltrate; and (6) Lyophilization: the ultrafiltrate obtained from Step (5) is lyophilized to yield magnesium hydroxysafflor yellow A. If necessary, the refined product of magnesium hydroxysafflor yellow A obtained from Step (6) is dissolved in water for injection. The resulting solution is filtered through a micropore film of 0.22 μm or an ultrafiltration membrane of MWCO 8000-10000 Daltons, and then transferred into bottles as aliquots. It is subsequently lyophilized to yield lyophilized powder for injection of magnesium hydroxysafflor yellow A.

The ion exchange resin described above is 001*7 ion exchange resin or macroporous HB-8 exchange resin; the macroporous resin separation uses macroporous adsorptive resin HZ801; the dextran gel chromatographic separation uses dextran gel LH-20; and the ultrafiltration uses ultrafiltration membrane of MWCO 8000-10000 Daltons.

As another objective of the present invention, usage of pharmaceutically acceptable salt of hydroxysafflor yellow A described above in preparation of medicine is provided, wherein the medicine has efficacy against platelet aggregation induced by PAF or ADP, and is intended to be used for treating or preventing diseases involving injury due to myocardial ischemia, cerebral ischemia or thrombosis. Dose of clinical use of the pharmaceutically acceptable salt of hydroxysafflor yellow A in the present invention is 50-200 mg/day.

The present invention uses saffron herbs as the raw material to prepare a new monomer medicine, pharmaceutically acceptable salt of hydroxysafflor yellow A. Its purity is guaranteed to be over 98%, and number of impurities is controlled to less than 5. It will become a new monomer compound which is superior as compared to hydroxysafflor yellow A with regard to safety, efficacy, stability and controllability when used to treat various blood circulation disorders such as coronary heart disease, angina, stroke, etc.

During study, through repeated trials, the present invention found that, hydroxysafflor yellow A does not present in acid form in saffron herbs extract. Currently available technologies (e.g., CN101168539A, CN1895317A, CN101195647A) adjust pH through adding pH value regulator such as sodium hydroxide directly into hydroxysafflor yellow extract, and hydroxysafflor yellow A will not convert into pharmaceutically acceptable salt of hydroxysafflor yellow A, therefore no monomer compound of pharmaceutically acceptable salt of hydroxysafflor yellow A could be obtained. Surprisingly, the present invention found that, hydroxysafflor yellow extract could actually be converted into hydroxysafflor yellow A through strongly acidic H-type cation exchange resin first, i.e. the acid form, then the pH is adjusted with different bases, corresponding salt of hydroxysafflor yellow A could be obtained through conversion, thus a single monomer compound of pharmaceutically acceptable salt of hydroxysafflor yellow A could be produced. Similarly, the present invention also found that, hydroxysafflor yellow A may be prepared first through acidification with refined product of hydroxysafflor yellow, then hydroxysafflor yellow A is salified with potassium hydroxide, ammonium hydroxide, magnesium hydroxide, calcium hydroxide, magnesium carbonate or calcium carbonate. In such case, monomer compound of pharmaceutically acceptable salt of hydroxysafflor yellow A described in the present invention may also be obtained with a high yield and at a high purity. Compared to hydroxysafflor yellow A, pharmaceutically acceptable salt of hydroxysafflor yellow A of the present invention has not only higher purity, over 98%, with the number of impurities being controlled to less than 5, but also better stability.

I. Pharmacodynamic Studies

Pharmacodynamic Study I:
Protection of Salt of Hydroxysafflor Yellow A Against Acute Myocardial Infarction Among Rats
Test Material
  Hydroxysafflor yellow for injection (50 mg/vial), source: Yongning Pharma, content: 50 mg/vial, containing 42.5 mg of hydroxysafflor yellow A;
  Potassium hydroxysafflor yellow A (prepared following Embodiment 1);
  Calcium hydroxysafflor yellow A (prepared following Embodiment 5).
Animals: 32 male SD rats, body weight 250-350 g.
Study Grouping and Dose Setup:

| Group | Animals | dose |
| --- | --- | --- |
| 1. Normal saline | 8 | 1 ml/kg |
| 2. Hydroxysafflor yellow for injection | 8 | 40 mg/kg |
| 3. Potassium hydroxysafflor yellow A | 8 | 40 mg/kg |
| 4. Calcium hydroxysafflor yellow A | 8 | 40 mg/kg |

Test method
1. Preparation of rat acute myocardial infarction model:
   Intraperitoneal anesthesia was performed with 3% sodium pentobarbital, 45 mg/kg. Right femoral artery and vein catheter were inserted for blood pressure monitoring and intravenous administration, respectively. Artificial mechanical ventilation was given through tracheal intubation at a rate of 60 times/min, and with a ventilation volume of about 10 ml/kg. Electrocardiogram (ECG) was recorded by placing needle electrode in limbs. A longitudinal skin incision was made approximately 0.5 cm to left sternal border, followed by blunt dissection of the subcutaneous tissue. The pectoralis major, pectoralis minor, and the intercostal muscle were dissected, ligated and cut with scissors successively. The chest was open from the fourth intercostal space along the left sternal border where apical beat is most significant. Cut the pericardium open with scissors, and clamp the pericardium to bilateral chest wall with hemostatic forceps, to form a pericardial bed and expose vessels on the surface of the left ventricle. 6-0 silk suture was threaded through superficial layer of myocardium (i.e. the anterior descending coronary artery) about 2 mm under the left auricle. The subject was stabilized for 15 min after threading. In case arrhythmia occurred or systolic arterial pressure was lower than 70 mmHg (9.31 KPa) over 5 min during this period, then the animal was excluded. Medicine was given intravenously 15 min after threading, the coronary was ligated 10 min after medication, and the ligation lasted for 4 hours.

2. Arrhythmia ranking: The severity of arrhythmia which occurred within 30 min after coronary ligature was scored.
3. Myocardial enzyme test: At the end of test, 2 ml of venous blood was taken, and centrifuged under 4° C. and 4000/min for 5 min. The supernatant was taken for myocardial enzyme test. Test items: LDH, AKP, CK.
4. Measurement of myocardial infarcted area: 4 h after coronary ligature, puncture was performed to the anterior wall of the left ventricle, and carbon ink was injected. Then the animal was sacrificed, and the heart was removed and cleaned with normal saline. Blood and non-myocardial tissue such as vessel and fat were removed. Moisture was dried with absorbent paper. Then the heart was weighed. The heart was cut into sections of about 2 mm from cardiac apex to the base of heart parallel. The perfusion area (perfused with ink) and area at high risk of ischemia (without ink perfusion). The area at high risk of ischemia was weighed and put into 0.05% NBT solution, and stained in a thermostatic water bath tank at 37° C. for 15 min NBT could stain matrix, coenzyme and deoxidation enzyme into blue, whereas in necrotic tissue, these metabolic matric and enzymes were lost, and it would not be colored. It could be observed that nonobstructive area was stained into deep blue, whereas the obstructive area was not stained. The nonobstructive heart muscle stained was cut off with scissors, and the non-stained infarcted heart muscle was weighed, to calculate percentage of infarcted heart muscle in the area of heart muscle at risk by weight (weight of infarction area/weight of area at risk*100%).

Statistical Analysis:

All the test data was expressed as mean±standard deviation, statistical test was done with analysis of variance (ANOVA), and the difference was considered significant if P<0.05.

i. Effect on Arrhythmia After Acute Myocardial Ischemia Among Rats 5 min after coronary ligature, rats began to experience arrhythmia, and it persisted till 30 min and peeked at around 10 min Findings of this test showed, hydroxysafflor yellow, potassium hydroxysafflor yellow A and calcium hydroxysafflor yellow A given intravenously could all reduce the severity of arrhythmia, however, potassium hydroxysafflor yellow A and calcium hydroxysafflor yellow A were more effective.

Arrhythmia Ranking in Each Study Group

| Group | n | Arrhythmia ranking |
| --- | --- | --- |
| Normal saline | 8 | 3.25 ± 0.7 |
| Hydroxysafflor yellow for injection | 8 | 1.63 ± 0.7* |
| Potassium hydroxysafflor yellow A | 8 | 1.38 ± 0.5* |
| Calcium hydroxysafflor yellow A | 8 | 1.46 ± 0.3* |

*P < 0.05 vs Group 1 ii. Comparison of Hydroxysafflor Yellow, Potassium Hydroxysafflor Yellow A and Calcium Hydroxysafflor Yellow A Regarding Effect on Extent of Myocardial Infarction Among Rats Effect on Extent of Myocardial Infarction in Each Study Group

| Group | n | Whole heart weight (g) | Infarction area (g) | Infarction rate (%) |
| --- | --- | --- | --- | --- |
| Normal saline | 8 | 0.38 ± 0.06 | 0.20 ± 0.04 | 52 ± 7 |
| Hydroxysafflor yellow for injection | 8 | 0.35 ± 0.04 | 0.11 ± 0.03* | 31 ± 8* |
| Potassium hydroxysafflor yellow A | 8 | 0.39 ± 0.07 | 0.10 ± 0.02* | 26 ± 9* |
| Calcium hydroxysafflor yellow A | 8 | 0.38 ± 0.05 | 0.11 ± 0.04* | 29 ± 6* |

*P < 0.05 vs Group 1 iii. Effect of Hydroxysafflor Yellow for Injection on Serum LDH, AKP, CK after Myocardial Infarction Among Rats Results of this study showed, hydroxysafflor yellow, potassium hydroxysafflor yellow A and calcium hydroxysafflor yellow A for injection given intravenously could all prevent serum LDH and CK of rats from increasing, however, potassium hydroxysafflor yellow A and calcium hydroxysafflor yellow A demonstrated more significant efficacy.

Serum LDH, AKP, CK Value in Each Study Group

| Group | n | LDH (IU/L) | AKP (IU/L) | CK (IU/L) |
| --- | --- | --- | --- | --- |
| Normal saline | 8 | 897 ± 134 | 159 ± 22 | 5218 ± 1203 |
| Hydroxysafflor yellow for injection | 8 | 496 ± 88* | 149 ± 27 | 2543 ± 678* |
| Potassium hydroxysafflor yellow A | 8 | 451 ± 78* | 144 ± 19 | 2203 ± 530* |
| Calcium hydroxysafflor yellow A | 8 | 463 ± 65* | 152 ± 24 | 2139 ± 594* |

*P < 0.05 vs Group 1

Study Conclusion

1. Hydroxysafflor yellow, potassium hydroxysafflor yellow A and calcium hydroxysafflor yellow A for injection could all reduce the severity of arrhythmia after coronary ligature among rats, however, potassium hydroxysafflor yellow A and calcium hydroxysafflor yellow A were more effective;
2. Compared to hydroxysafflor yellow for injection, potassium hydroxysafflor yellow A and calcium hydroxysafflor yellow A had better efficacy in terms of reducing the extent of myocardial infarction among rats;
3. Compared to hydroxysafflor yellow for injection, potassium hydroxysafflor yellow A and calcium hydroxysafflor yellow A showed better efficacy regarding the inhibition on serum LDH and CK among rats;
4. Potassium hydroxysafflor yellow A and calcium hydroxysafflor yellow A showed no significant difference regarding efficacy.

Pharmacodynamic Study II:

Intravenous injection of potassium hydroxysafflor yellow A and calcium hydroxysafflor yellow A showed preventive effect on acute cerebral ischemia.

Test Material

Hydroxysafflor yellow for injection (50 mg/vial), source: Yongning Pharma, content: 50 mg/vial, containing 42.5 mg of hydroxysafflor yellow A;

Potassium hydroxysafflor yellow A (prepared following Embodiment 1);

Calcium hydroxysafflor yellow A (prepared following Embodiment 5);

The study is described as following:

1. Selectivity of isolated heart and cerebral vessel from dogs: During this study, Willis arteries and coronary ring from beagles were mounted on ex vivo vascular measuring device. Adjust the tension sensor, and add 10-6 mol/L phenylephrine into the liquid in bath cup, so as to maintain vascular tension. And then add potassium hydroxysafflor yellow A or calcium hydroxysafflor yellow A for injection at a dose of 10 mg/ml into the liquid in bath cup every 5 min, until the vascular ring reaction was weak, or no more reaction occurred (usually medicine was added 4-5 times). Calculate vasoconstriction or vasodilation change value. Study results showed: Dilation of potassium hydroxysafflor yellow A for injection on cardiac vascular ring was 31.6%, whereas that on cerebral vascular ring was 73.1%; dilation of calcium hydroxysafflor yellow A for injection on cardiac vascular ring was 37.1%, whereas that on cerebral vascular ring was 69.7%. It indicated that both potassium hydroxysafflor yellow A and calcium hydroxysafflor yellow A for injection had very good selectivity and dilation on cerebral vessel, and there was no significant difference between them.

2. Effect on acute cerebral ischemia: SD rats for study were given potassium hydroxysafflor yellow A or calcium hydroxysafflor yellow A intravenously, and then acute cerebral ischemia model was established using regular Longa's method for middle cerebral artery occlusion (MCAO). After kept for 24 h, rats were assessed for neuroethological ranking, and then decapitated. The brain was removed, placed into mold and cut into 7 sections. TTC staining was done. The living brain tissue became red, whereas the necrotic brain tissue was not colored. Percentage of necrotic brain tissue in cerebral hemisphere was calculated with image analysis software. Study results showed, area of cerebral infarction in the solvent control group was 38%, 15.7% in the nimodipine positive group, 38.2%, 27.6% and 21.9% in groups receiving low, medium and high dose of potassium hydroxysafflor yellow A for injection, respectively, and 41.3%, 25.7% and 21.6% in groups receiving low, medium and high dose of calcium hydroxysafflor yellow A for injection, respectively. Compared to solvent control, medium and high dose of potassium hydroxysafflor yellow A and calcium hydroxysafflor yellow A for injection could significantly reduce brain tissue necrosis due to acute cerebral ischemia, and there was no significant difference between them.

3. Effect on vasopermeability in rats: Rats were injected intravenously, once per day, for 7 days. After the last dose, rats were anesthetized, injected intravenously with Evans blue 50 mg/kg. After 5 minutes, bilateral common carotid arteries were ligated. The animals were sacrificed by decapitation after 3 hours. The brain was removed, weighed and immersed in formamide solution. It was placed in an incubator at 45° C. for 72 h. During this period, Evans blue in the cerebral vessel could be leached out into formamide solution. Testing the amount of Evans blue leached out into the formamide solution with spectrophotometer could indicate permeability of cerebral vessel. Study results showed, potassium hydroxysafflor yellow A and calcium hydroxysafflor yellow A for injection has a very significant effect of reducing Evans blue being leached out from cerebral vessel in the high and medium dose groups. This indicated that this medicine had good efficacy in terms of decreasing vasopermeability. And there was no significant difference between these two medicines.

4. Effect on cerebral blood flow of dog: Beagles were used as the study animal. After the dog was anesthetized with sodium pentobarbital, external jugular vein, internal jugular vein and vertebral artery were isolated surgically. The external jugular vein was ligated. Flow probes were placed in internal jugular vein and vertebral artery. Two times of the total blood flow recorded by both probes represented blood supply of the whole brain. At the end of the study, the brain was removed and weighed to calculate blood flow per 100 g of brain tissue. The study results showed, medium and high dose of both potassium hydroxysafflor yellow A and calcium hydroxysafflor yellow A for injection could significantly increase blood flow after being given intravenously, however, they could only maintain the blood flow for a short time (about 15 min) This study indicated, intravenous infusion should be selected as the administration method to treat acute cerebral ischemia in future clinical practice, and there was no significant different between these two medicines.

5. Effect on acute cerebral anoxia: A study was carried out using Kunming mice rats. The animals were kept in an environment lacking oxygen. The survival duration was recorded to examine whether resistance to acute hypoxia was increased after animals given the medicine. The study finding showed, in a closed vessel, mice in the solvent control group survived 32 min, whereas mice from those three groups receiving low, medium and high doses of potassium hydroxysafflor yellow A for injection survived 36, 37, and 36 min, respectively; mice from those three groups receiving low, medium and high doses of calcium hydroxysafflor yellow A for injection survived 35, 38, and 37 min, respectively. Statistical analysis showed significant difference as compared with the control group (P<0.05–0.01). Study on rat was carried out in an environment containing 97% of nitrogen and 3% of oxygen. Animals were kept in the container until respiration ceased. Survival duration of each group was, 3 minutes 43 seconds in the solvent control group; 5 minutes 38 seconds in the positive control group (nimodipine). There was very significant difference between them. Those three groups receiving low, medium and high doses of potassium hydroxysafflor yellow A for injection were 3 minutes 20 seconds, 4 minutes 30 seconds, and 4 minutes 9 seconds; those three groups receiving low, medium and high doses of calcium hydroxysafflor yellow A for injection were 3 minutes 31 seconds, 4 minutes 35 seconds, and 4 minutes 21 seconds. As compared to the solvent control group, survival duration in the groups receiving high dose of potassium hydroxysafflor yellow A for injection and calcium hydroxysafflor yellow A for injection was significantly increased, and there was no significant difference between them.

6. Anti-platelet aggregation: The study included two stages, instrument testing and in vivo test. 1) Instrument testing method: The rabbit was given potassium hydroxysafflor yellow A intravenously, once per day, for 5 days. 4 ml of blood was taken from heart 2 hours after the last dose. The blood was centrifuged under a low speed to obtain platelet-rich serum; and centrifuged under a high speed to obtain serum lacking platelet. Adenosine diphosphate (ADP) and platelet-activating factor (PAF) were chosen as the platelet aggregation inducing agent. And platelet aggregometer was used for testing. In study of potassium hydroxysafflor yellow A solution for injection against platelet aggregation induced by ADP and PAF, both of them showed very good anti-platelet aggregation effect. And good dose-effect relationship was demonstrated between the three doses. 2) In vivo method: An arteriovenous short was created with latex tubing in rats. There was surgical silk mounted in the latex tubing. Using characteristics of platelet adhesion, the short was opened to allow blood to flow trans-arteriovenously through the latex tubing. And then silk was removed and weighed. The weight of platelet adhered to the silk was calculated by subtracting the dry weight. Study results showed, weight of platelet adhered on the silk was 14.8±1.57 mg in the solvent control group; 8.62±2.79 mg in the positive control group; 13.6±1.89 mg, 9.90±1.53 mg and 8.91±1.34 mg in three groups receiving low, medium and high doses of potassium hydroxysafflor yellow A for injection, respectively; 13.9±1.54 mg, 10.26±1.15 mg and 8.73±1.79 mg in three groups receiving low, medium and high doses of calcium hydroxysafflor yellow A for injection. There was very significant difference when comparing the groups receiving medium and high dose of potassium hydroxysafflor yellow A and calcium hydroxysafflor yellow A for injection with the solvent control group. It indicated that both potassium hydroxysafflor yellow A and calcium hydroxysafflor yellow A for injection had very good effect against platelet aggregation, and there was no significant difference between them.

7. Effect on blood viscosity: Rabbit was treated intravenously, once per day, for 5 days. 2 hours after the last dose, blood was taken from heart and anticoagulated, and tested with blood rheometer directly. The study results showed, as compared to the solvent control group, all three indexes including low shear, medium shear and high shear of blood viscosity in groups receiving potassium hydroxysafflor yellow A and calcium hydroxysafflor yellow A decreased as dose increased. And the extent of decrease was increased as dose increasing. Effect of high dose groups receiving both medicines was superior to the positive control group receiving nimodipine solution for injection. It indicated that potassium hydroxysafflor yellow A and calcium hydroxysafflor yellow A for injection had significant effect in terms of decreasing blood viscosity, and there was no significant difference between them.

II. Stability Study and Physico-Chemical Data (I) Observation on stability of hydroxysafflor yellow A salts and hydroxysafflor yellow A
Test Material
Hydroxysafflor yellow A, Homemade following CN102675379A, purity 89.9%;
Hydroxysafflor yellow A, Prepared by acidification following this patent, purity 99.2%;
Ammonium hydroxysafflor yellow A, Homemade (prepared following Embodiment 3), purity 99.3%;
Potassium hydroxysafflor yellow A, Homemade (prepared following Embodiment 1), purity 98.5%;
Calcium hydroxysafflor yellow A, Homemade (prepared following Embodiment 5), purity 98.8%;
Magnesium hydroxysafflor yellow A, Homemade (prepared following Embodiment 8), purity 99.0%;
Triethylamine hydroxysafflor yellow A, Homemade (prepared following Embodiment 10), purity 99.0%;
Tetramethylammonium hydroxysafflor yellow A, Homemade (prepared following Embodiment 11), purity 99.0%;

| | Item | Accelerated 0 month | Accelerated 1 month | Accelerated 2 months | Accelerated 3 months |
|---|---|---|---|---|---|
| hydroxysafflor yellow A (Homemade following CN102675379A) | Total purity | 10.1% | 13.9% | 19.8% | 28.6% |
| | Content | 89.8% | 84.0% | 81.4% | 70.1% |
| hydroxysafflor yellow A (Prepared by acidification following this patent) | Total purity | 0.8% | 5.9% | 10.7% | 18.6% |
| | Content | 99.1% | 94.1% | 89.2% | 81.3% |
| Ammonium hydroxysafflor yellow A | Total purity | 0.7% | 1.1% | 1.8% | 2.7% |
| | Content | 96.8% | 96.2% | 95.5% | 94.6% |
| Potassium hydroxysafflor yellow A | Total purity | 1.5% | 1.8% | 2.2% | 2.8% |
| | Content | 92.5% | 92.2% | 91.8% | 91.3% |
| Calcium hydroxysafflor yellow A | Total purity | 1.2% | 1.4% | 1.9% | 2.6% |
| | Content | 96.2% | 95.6% | 95.1% | 94.5% |
| Magnesium hydroxysafflor yellow A | Total purity | 1.0% | 1.3% | 1.8% | 2.4% |
| | Content | 97.4% | 97.0% | 96.4% | 95.8% |
| Triethylamine hydroxysafflor yellow A | Total purity | 1.0% | 1.6% | 2.4% | 3.2% |
| | Content | 84.9% | 84.4% | 83.7% | 82.8% |
| Tetramethylammonium hydroxysafflor yellow A | Total purity | 1.0% | 1.5% | 2.3% | 3.1% |
| | Content | 88.3% | 87.8% | 87.1% | 86.3% |

Note:
Content is calculated as hydroxysafflor yellow A.

Study results showed, stability comparison between monomer compound of pharmaceutically acceptable salt of hydroxysafflor yellow A and hydroxysafflor yellow A indicated that pharmaceutically acceptable salt of hydroxysafflor yellow A was superior regarding stability.

(II) Observation on Physico-Chemical Data of Hydroxysafflor Yellow A Salts and Hydroxysafflor Yellow A.

Results of physico-chemical data of pharmaceutically acceptable salt of hydroxysafflor yellow A

| Sample | pH | Solubility |
|---|---|---|
| Hydroxysafflor yellow A | 1.9 | Slightly soluble |
| Ammonium hydroxysafflor yellow A | 4.5 | Easily soluble |
| Potassium hydroxysafflor yellow A | 5.8 | Easily soluble |
| Calcium hydroxysafflor yellow A | 5.5 | Easily soluble |

-continued

| Sample | pH | Solubility |
|---|---|---|
| Magnesium hydroxysafflor yellow A | 5.2 | Easily soluble |
| Triethylamine hydroxysafflor yellow A | 4.5 | Easily soluble |
| Tetramethylammonium hydroxysafflor yellow A | 4.7 | Easily soluble |

Test results showed that, comparison of physico-chemical data between monomer compound of pharmaceutically acceptable salt of hydroxysafflor yellow A and hydroxysafflor yellow A indicated pharmaceutically acceptable salt of hydroxysafflor yellow A was superior in terms of tolerance.

DETAILED DESCRIPTION OF THE PREFERRED EMBODIMENT

Embodiment 1

Figure 1:
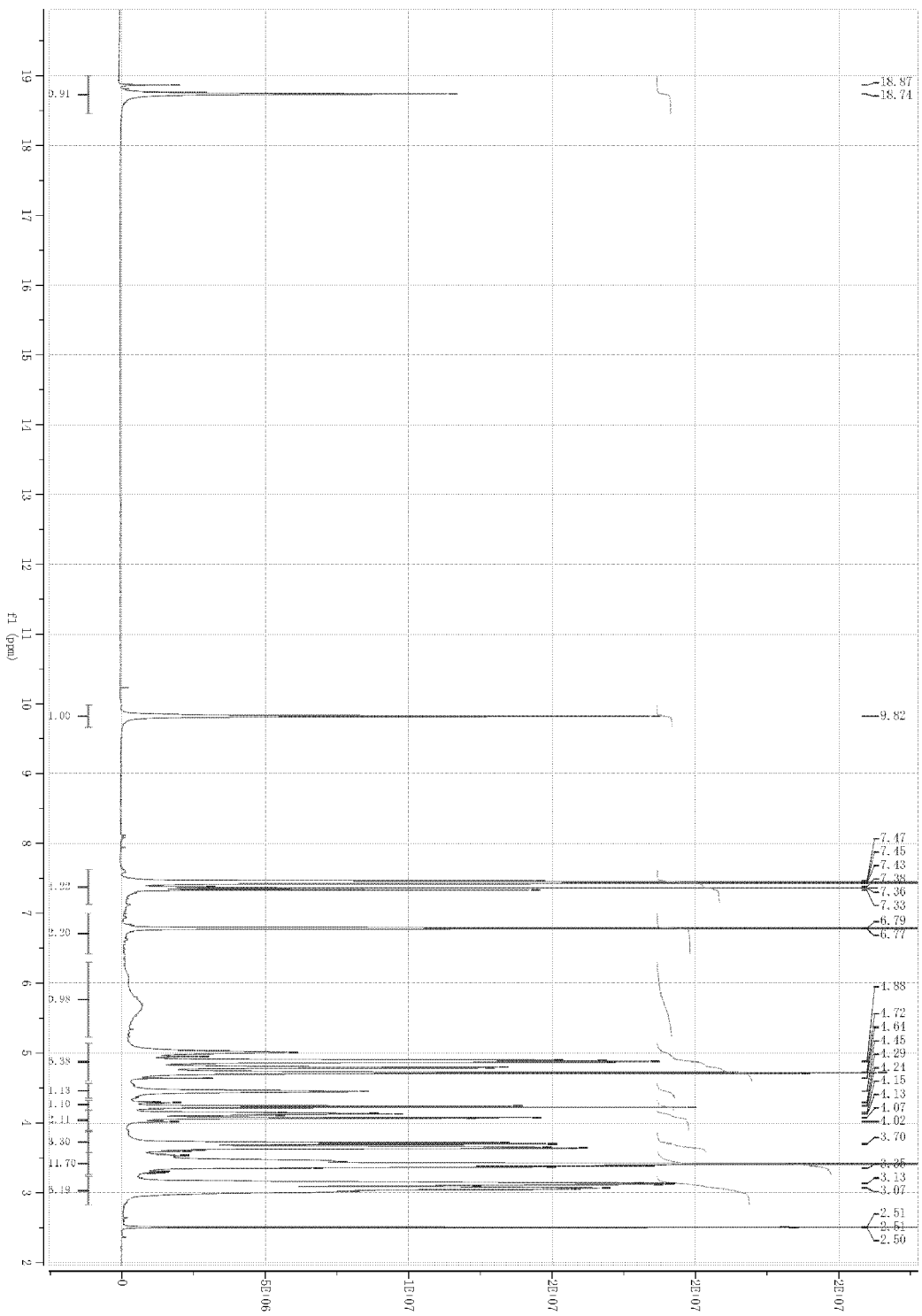
FIG. 1: $^1$H-NMR of calcium hydroxysafflor yellow A of formula (IV)

Potassium Hydroxysafflor Yellow A (Compound of Formula II of the Present Invention)

Weigh certain amount of safflower, add deionized water that is 12.5 times of weight of crude drug, extract under a temperature of 100° C. for 20-25 minutes, and filter. Add deionized water that is 10 times of weight of crude drug into the resid, repeat extraction under conditions described above, and filter. Pool the extract from the two steps above, and allow it to cool to ambient temperature. After centrifuging with centrifuge, the centrifugate is taken for further use. The centrifugate above is added into preconditioned 001*7 strongly acidic H-type cation exchange resin, with ratio of diameter to height of column being 1:10 and column volume being 500 ml, under a flow rate of 3 ml/min. The effluent is collected. Add the same moles of potassium hydroxide as calculated as hydroxysafflor yellow A. Then the resulting solution is slowly added into macroporous adsorptive resin separation column, with ratio of diameter to height of column being 1:12 and a sample injection flow of 10 ml per minute. When sample injection is completed, elute with deionized water under room temperature at a flow rate of 20 ml per minute. The eluent is concentrated at 60° C. and reduced pressure to yield a concentrated solution of crude potassium hydroxysafflor yellow A. When calculated as safflower, each kilogram of safflower could yield 100 ml of concentrated solution. The concentrated solution of crude potassium hydroxysafflor yellow A undergoes gel LH-20 column, with ratio of diameter to height of column being 1:5 and sample injection volume being 10% of bed volume, at an elution flow rate of 5 ml per minute. And the part containing potassium hydroxysafflor yellow A is collected. The solution collected is concentrated at 60° C. and reduced pressure to yield a concentrated solution of refined product of potassium hydroxysafflor yellow A. When calculated as safflower, each kilogram of safflower could yield 35-50 ml of concentrated solution. It is subsequently lyophilized to yield an amber powder of refined product of potassium hydroxysafflor yellow A. Its purity is 98.5%. As calculated as safflower, the yield is around 0.55%.

The infrared (IR) spectrum, mass-spectrum (MS), $^1$H-NMR, and $^{13}$C-NMR data of Potassium hydroxysafflor yellow A is as following:

1. Infrared Absorption Spectrum
Instrument model: Bruker model VECTOR-22 infrared absorption spectrometer
IR (Potassium Bromide Pellet)

| Absorption peak (cm$^{-1}$) | Vibration type | Group | Intensity |
|---|---|---|---|
| 3361 | $\upsilon_{-OH}$ | —OH | br, s |
| 1650 | $\upsilon_{C=O}$ | —C=O | s |
| 1624 | $\upsilon_{C=C}$ | —C=C— | s |
| 1604, 1515 | $\upsilon_{C=C}$ | $C_6H_6$ | s |
| 1440 | $\delta_{-CH2}$ | —CH$_2$ | m |
| 1171, 1077, 1005 | $\upsilon_{C-O}$ | —C—OH | s |

2. Mass-Spectrum
Instrument model: LCQ-DECAXP (FINNIGAN Corporation, USA)
Testing condition: ESI
MS
+c ESI 651.06 (M)$^-$
−c ESI 611.24 (M-K)$^-$
3. $^1$H-NMR and $^{13}$C-NMR
Instrument model: BRUCKER AVANCE III Model 500 superconducting nuclear magnetic resonance analyzer
Testing condition: solvent: DMSO, internal standard: TMS $^1$H-NMR Data of Potassium Hydroxysafflor Yellow A

| Proton order (H attribution) | Chemical shift δ (ppm) | Proton number |
|---|---|---|
| 8 | 7.27 | 1 |
| 9 | 7.39 | 1 |
| 11, 15 | 7.41 | 2 |
| 12, 14 | 6.75 | 2 |
| 3-OH | 18.65 | 1 |
| 4-OH | 4.71 | 1 |
| 5-OH | Disappeared | Substituted |
| 13-OH | 9.75 | 1 |
| Saccharide part | | |
| G1 | 3.61 | 1 |
| G2 | 2.84 | 1 |
| G3 | 3.06 | 1 |
| G4 | 3.27 | 1 |
| G5 | 3.01 | 1 |
| G6 | 3.36-3.25 | 2 |
| G'1 | 4.14 | 1 |
| G'2 | 4.03 | 1 |
| G'3 | 3.08 | 1 |
| G'4 | 3.04 | 1 |
| G'5 | 2.92 | 1 |
| G'6 | 3.58 | 2 |
| Hydroxyl on saccharide | 4.41-4.79 | 8 |

13C-NMR Data of Hydroxysafflor Yellow A Potassium Salt

| Carbon order | Chemical shift (ppm) |
| --- | --- |
| 1 | 189.6 |
| 2 | 106.7 |
| 3 | 195.9 |
| 4 | 86.1 |
| 5 | 183.2 |
| 6 | 99.7 |
| 7 | 179.3 |
| 8 | 123.9 |
| 9 | 135.9 |
| 10 | 127.9 |
| 11(15) | 129.7 |
| 12(14) | 116.0 |
| 13 | 158.8 |
| G1 | 85.9 |
| G2 | 70.4 |
| G3 | 78.8 |
| G4 | 70.3 |
| G5 | 81.2 |
| G6 | 61.7 |
| G'1 | 74.4 |
| G'2 | 69.2 |
| G'3 | 79.7 |
| G'4 | 71.6 |
| G'5 | 80.8 |
| G'6 | 62.2 |

The refined product of potassium hydroxysafflor yellow A prepared is dissolved in water for injection. The resulting solution is filtered through a micropore film of 0.22 μm or an ultrafiltration membrane of MWCO 8000-10000 Daltons, and then transferred into bottles as aliquots. It is subsequently lyophilized to yield lyophilized powder for injection of potassium hydroxysafflor yellow A.

Embodiment 2

Potassium Hydroxysafflor Yellow A (Compound of Formula II of the Present Invention)

Weigh certain amount of safflower, add deionized water that is 12.5 times of weight of crude drug, extract under a temperature of 100° C. for 20-25 minutes, and filter. Add deionized water that is 10 times of weight of crude drug into the resid, repeat extraction under conditions described above, and filter. Pool the extract from the two steps above, and allow it to cool to ambient temperature. After centrifuging with centrifuge, the centrifugate is taken for further use. The centrifugate above is added into preconditioned HB-8 macroporous strongly acidic H-type cation exchange resin, with ratio of diameter to height of column being 1:10 and column volume being 500 ml, under a flow rate of 3 ml/min. The effluent is collected. Add the same moles of potassium hydroxide as calculated as hydroxysafflor yellow A. Then the resulting solution is slowly added into macroporous adsorptive resin separation column, with ratio of diameter to height of column being 1:12 and a sample injection flow of 10 ml per minute. When sample injection is completed, elute with deionized water under room temperature at a flow rate of 20 ml per minute. The eluent is concentrated at 60° C. and reduced pressure to yield a concentrated solution of crude potassium hydroxysafflor yellow A. When calculated as safflower, each kilogram of safflower could yield 100 ml of concentrated solution. The concentrated solution of crude potassium hydroxysafflor yellow A undergoes gel LH-20 column, with ratio of diameter to height of column being 1:5 and sample injection volume being 10% of bed volume, at an elution flow rate of 5 ml per minute. And the part containing potassium hydroxysafflor yellow A is collected. The solution collected is concentrated at 60° C. and reduced pressure to yield a concentrated solution of refined product of potassium hydroxysafflor yellow A. When calculated as safflower, each kilogram of safflower could yield 35-50 ml of concentrated solution. It is subsequently lyophilized to yield an amber powder of refined product of potassium hydroxysafflor yellow A. The purity is 98.6%. As calculated as safflower, the yield is around 0.50%.

Embodiment 3

Ammonium Hydroxysafflor Yellow A of Formula III (Compound of Formula III of the Present Invention)

Weigh certain amount of safflower, add deionized water that is 12.5 times of weight of crude drug, extract under a temperature of 100° C. for 20-25 minutes, and filter. Add deionized water that is 10 times of weight of crude drug into the resid, repeat extraction under conditions described above, and filter. Pool the extract from the two steps above, and allow it to cool to ambient temperature. After centrifuging with centrifuge, the centrifugate is taken for further use. The centrifugate above is added into preconditioned 001*7 strongly acidic H-type cation exchange resin, with ratio of diameter to height of column being 1:10 and column volume being 500 ml, under a flow rate of 3 ml/min. The effluent is collected. Add the same moles of ammonia as calculated as hydroxysafflor yellow A. Then the resulting solution is slowly added into macroporous adsorptive resin separation column, with ratio of diameter to height of column being 1:12 and a sample injection flow of 10 ml per minute. When sample injection is completed, elute with deionized water under room temperature at a flow rate of 20 ml per minute. The eluent is concentrated at 60° C. and reduced pressure to yield a concentrated solution of crude ammonium hydroxysafflor yellow A. When calculated as safflower, each kilogram of safflower could yield 100 ml of concentrated solution. The concentrated solution of ammonium hydroxysafflor yellow A undergoes gel LH-20 column, with ratio of diameter to height of column being 1:5 and sample injection volume being 10% of bed volume, at an elution flow rate of 5 ml per minute. And the part containing ammonium hydroxysafflor yellow A is collected. The solution collected is concentrated at 60° C. and reduced pressure to yield a concentrated solution of refined product of ammonium hydroxysafflor yellow A. When calculated as safflower, each kilogram of safflower could yield 35-50 ml of concentrated solution. It is subsequently lyophilized to yield an amber powder of refined product of ammonium hydroxysafflor yellow A. The purity is 99.3%. As calculated as safflower, the yield is around 0.45%.

The infrared (IR) spectrum, mass-spectrum (MS), $^1$H-NMR, and $^{13}$C-NMR data of Potassium hydroxysafflor yellow A is as following:

1. Infrared Absorption Spectrum
Instrument Model: Bruker Model VECTOR-22 Infrared Absorption Spectrometer
IR (Potassium Bromide Pellet)

| Absorption peak ($cm^{-1}$) | Vibration type | Group | Intensity |
| --- | --- | --- | --- |
| 3361 | $\upsilon_{-OH}$ | —OH | br, s |
| 1651 | $\upsilon_{C=O}$ | —C=O | s |
| 1624 | $\upsilon_{C=C}$ | —C=C— | s |

| Absorption peak (cm$^{-1}$) | Vibration type | Group | Intensity |
|---|---|---|---|
| 1604, 1515 | $\upsilon_{C=C}$ | $C_6H_6$ | s |
| 1441 | $\delta_{-CH2}$ | —CH$_2$ | m |
| 1171, 1077, 1005 | $\upsilon_{C-O}$ | —C—OH | s |

2. Mass-Spectrum
Instrument Model: LCQ-DECAXP (FINNIGAN Corporation, USA)
Testing Condition: ESI
MS
+c ESI 613.17 (M)$^-$
−c ESI 611.22 (M-H)$^-$
3. $^1$H-NMR and $^{13}$C-NMR
Instrument Model: BRUCKER AVANCE III Model 500 Superconducting Nuclear Magnetic Resonance Analyzer
Testing Condition: Solvent: DMSO, Internal Standard: TMS $^1$H-NMR Data of Ammonium Hydroxysafflor Yellow A

| Proton order (H attribution) | Chemical shift δ (ppm) | Proton number |
|---|---|---|
| 8 | 7.26 | 1 |
| 9 | 7.39 | 1 |
| 11, 15 | 7.40 | 2 |
| 12, 14 | 6.76 | 2 |
| 3-OH | 18.65 | 1 |
| 4-OH | 4.76 | 1 |
| 5-ONH4 | 6.99-7.23 | 4 |
| 13-OH | 9.74 | 1 |
| Saccharide part | | |
| G1 | 3.61 | 1 |
| G2 | 2.81 | 1 |
| G3 | 3.06 | 1 |
| G4 | 3.27 | 1 |
| G5 | 3.00 | 1 |
| G6 | 3.35-3.24 | 2 |
| G'1 | 4.15 | 1 |
| G'2 | 4.04 | 1 |
| G'3 | 3.06 | 1 |
| G'4 | 3.04 | 1 |
| G'5 | 2.91 | 1 |
| G'6 | 3.60 | 2 |
| Hydroxyl on saccharide | 4.41~4.77 | 8 |

$^{13}$C-NMR Data of Ammonium Hydroxysafflor Yellow A

| Carbon order | Chemical shift (ppm) |
|---|---|
| 1 | 189.3 |
| 2 | 107.0 |
| 3 | 196.0 |
| 4 | 86.1 |
| 5 | 183.7 |
| 6 | 189.2 |
| 7 | 179.0 |
| 8 | 123.8 |
| 9 | 135.9 |
| 10 | 127.9 |
| 11(15) | 129.7 |
| 12(14) | 116.0 |
| 13 | 158.8 |
| G1 | 85.8 |
| G2 | 70.5 |
| G3 | 78.9 |
| G4 | 70.4 |
| G5 | 81.2 |
| G6 | 61.9 |
| G'1 | 74.4 |
| G'2 | 69.2 |
| G'3 | 79.7 |
| G'4 | 71.7 |
| G'5 | 80.9 |
| G'6 | 62.3 |

Embodiment 4

Ammonium Hydroxysafflor Yellow A (i.e. Compound of Formula III of the Present Invention)

Weigh certain amount of safflower, add deionized water that is 12.5 times of weight of crude drug, extract under a temperature of 100° C. for 20-25 minutes, and filter. Add deionized water that is 10 times of weight of crude drug into the resid, repeat extraction under conditions described above, and filter. Pool the extract from the two steps above, and allow it to cool to ambient temperature. After centrifuging with centrifuge, the centrifugate is taken for further use. The centrifugate above is added into preconditioned HB-8 macroporous strongly acidic H-type cation exchange resin, with ratio of diameter to height of column being 1:10 and column volume being 500 ml, under a flow rate of 3 ml/min. The effluent is collected. Add the same moles of ammonia as calculated as hydroxysafflor yellow A. Then the resulting solution is slowly added into macroporous adsorptive resin separation column, with ratio of diameter to height of column being 1:12 and a sample injection flow of 10 ml per minute. When sample injection is completed, elute with deionized water under room temperature at a flow rate of 20 ml per minute. The eluent is concentrated at 60° C. and reduced pressure to yield a concentrated solution of crude ammonium hydroxysafflor yellow A. When calculated as safflower, each kilogram of safflower could yield 100 ml of concentrated solution. The concentrated solution of ammonium hydroxysafflor yellow A undergoes gel LH-20 column, with ratio of diameter to height of column being 1:5 and sample injection volume being 10% of bed volume, at an elution flow rate of 5 ml per minute. And the part containing ammonium hydroxysafflor yellow A is collected. The solution collected is concentrated at 60° C. and reduced pressure to yield a concentrated solution of refined product of ammonium hydroxysafflor yellow A. When calculated as safflower, each kilogram of safflower could yield 35-50 ml of concentrated solution. It is subsequently lyophilized to yield an amber powder of refined product of ammonium hydroxysafflor yellow A. The purity is 99.4%. As calculated as safflower, the yield is around 0.50%.

Embodiment 5

Calcium Hydroxysafflor Yellow A (Compound of Formula IV of the Present Invention)

Weigh certain amount of safflower, add deionized water that is 12.5 times of weight of crude drug, extract under a temperature of 100° C. for 20-25 minutes, and filter. Add deionized water that is 10 times of weight of crude drug into the resid, repeat extraction under conditions described above, and filter. Pool the extract from two steps above, and allow it to cool to ambient temperature. After centrifuging with centrifuge, the centrifugate is taken for further use. The centrifugate above is added into preconditioned 001*7 strongly acidic H-type cation exchange resin, with ratio of diameter to height of column being 1:10 and column volume being 500 ml, under a flow rate of 3 ml/min. The effluent is collected. Add half the moles of $Ca(OH)_2$ as calculated as hydroxysafflor yellow A. Then the resulting solution is slowly added into macroporous adsorptive resin separation column, with ratio of diameter to height of column being 1:12 and a sample injection flow of 10 ml per minute. When sample injection is completed, elute with deionized water under room temperature at a flow rate of 20 ml per minute. The eluent is concentrated at 60° C. and reduced pressure to yield a concentrated solution of crude calcium hydroxysafflor yellow A. When calculated as safflower, each kilogram of safflower could yield 100 ml of concentrated solution. The concentrated solution of calcium hydroxysafflor yellow A undergoes gel LH-20 column, with ratio of diameter to height of column being 1:5 and sample injection volume being 10% of bed volume, at an elution flow rate of 5 ml per minute. And the part containing calcium hydroxysafflor yellow A is collected. The solution collected is concentrated at 60° C. and reduced pressure to yield a concentrated solution of refined product of calcium hydroxysafflor yellow A. When calculated as safflower, each kilogram of safflower could yield 35-50 ml of concentrated solution. It is subsequently lyophilized to yield an amber powder of refined product of calcium hydroxysafflor yellow A. The purity is 98.8%. As calculated as safflower, the yield is around 0.50%.

MS, $^1$H-NMR, $^{13}$C-NMR data of calcium hydroxysafflor yellow A is as following:

1. MS

Instrument model: LCQ-DECAXP (FINNIGAN Corporation, USA)

Testing condition: ESI

MS

+c ESI 1263.08 $(M)^+$

−c ESI 611.29 $(M)^−$

2. $^1$H-NMR and $^{13}$C-NMR

Figure 2:
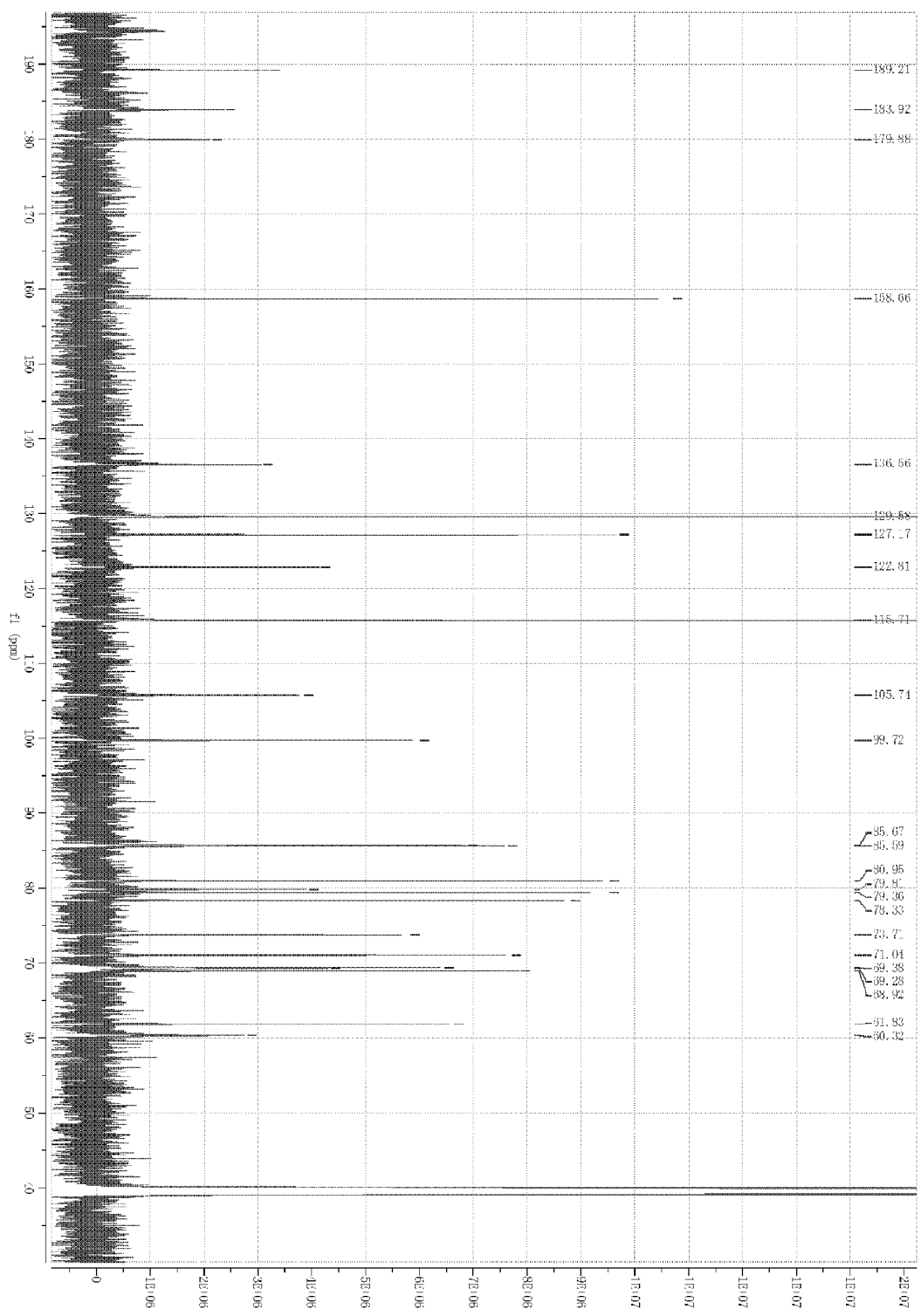
FIG. 2: $^{13}$C-NMR of calcium hydroxysafflor yellow A of formula (IV)

Instrument model: BRUCKER AVANCE III Model 500 superconducting nuclear magnetic resonance analyzer Testing condition: solvent: DMSO, internal standard: TMS See FIGS. 1 and 2 for results.

$^1$H-NMR Data Attribution of Calcium Hydroxysafflor Yellow A (Due to Symmetrical Structure, the Numbers are Consistent)

Chemical shift δ(ppm) 3.01-4.15 is attributed to hydrogen of saccharide part, G1-G6 and G'1-G'6; 4.29-4.88 is attributed to hydroxyl hydrogen on saccharide; 7.33 (1H), 7.38 (1H) are attributed to 8 and 9; 6.77-7.47 (4H) is attributed to 11-15; 18.74 (1H) is attributed to 3-OH; 4.72 (1H) is attributed to 4-OH; 9.82 (1H) is attributed to 13-OH.

$^{13}$C-NMR Data Attribution of Calcium Hydroxysafflor Yellow A

Chemical shift δ(ppm) 60.32 (1C), 61.83 (1C) (secondary carbon) are attributed to carbon of saccharide part, G6, G'6; 68.92, 69.28, 69.38, 71.04, 73.71, 78.33, 79.36, 79.81, 80.95, 85.67 (10C) (tertiary carbon) are attributed to carbon of saccharide part, G1-G5 and G'1-G'5; 115.71 (2C) (tertiary carbon) is attributed to 12 and 14; 129.58 (2C) (tertiary carbon) is attributed to 11 and 15; 122.81 (1C), 136.56 (1C) (tertiary carbon) are attributed to 8 and 9;

Chemical shift δ(ppm) 189.21, 105.74, 85.59, 183.92, 99.72 (5C) are attributed to 1-2, 4-6;

179.88 (1C), 127.17 (1C), 158.66 (1C) are attributed to 7, 10, 13, respectively.

The refined product of calcium hydroxysafflor yellow A prepared is dissolved in water for injection. The resulting solution is filtered through a micropore film of 0.22 μm or an ultrafiltration membrane of MWCO 8000-10000 Daltons, and then transferred into bottles as aliquots. It is subsequently lyophilized to yield lyophilized powder for injection of calcium hydroxysafflor yellow A.

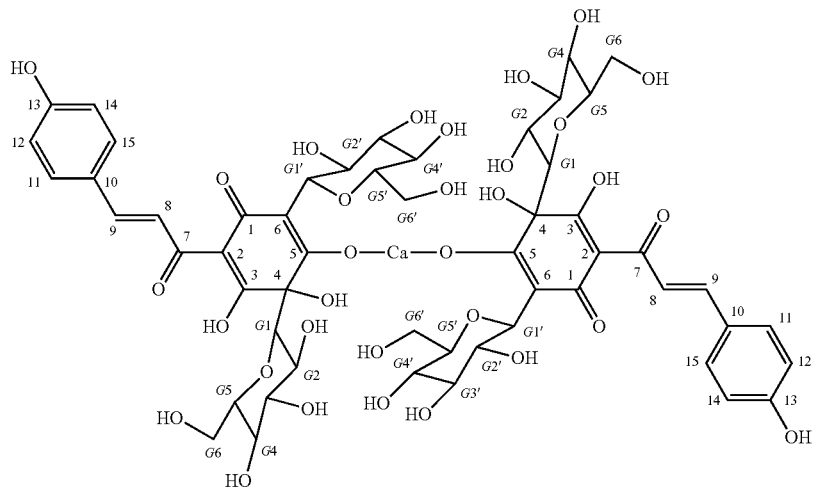

Embodiment 6

Calcium Hydroxysafflor Yellow A (Compound of Formula IV)

Weigh certain amount of safflower, add deionized water that is 12.5 times of weight of crude drug, extract under a temperature of 100° C. for 20-25 minutes, and filter. Add deionized water that is 10 times of weight of crude drug into the resid, repeat extraction under conditions described above, and filter. Pool the extract from the two steps above, and allow it to cool to ambient temperature. After centrifuging with centrifuge, the centrifugate is taken for further use. The centrifugate above is added into preconditioned HB-8 macroporous strongly acidic H-type cation exchange resin, with ratio of diameter to height of column being 1:10 and column volume being 500 ml, under a flow rate of 3 ml/min. The effluent is collected. Add half the moles of $Ca(OH)_2$ as calculated as hydroxysafflor yellow A. Then the resulting solution is slowly added into macroporous adsorptive resin separation column, with ratio of diameter to height of column being 1:12 and a sample injection flow of 10 ml per minute. When sample injection is completed, elute with deionized water under room temperature at a flow rate of 20 ml per minute. The eluent is concentrated at 60° C. and reduced pressure to yield a concentrated solution of crude calcium hydroxysafflor yellow A. When calculated as safflower, each kilogram of safflower could yield 100 ml of concentrated solution. The concentrated solution of calcium hydroxysafflor yellow A undergoes gel LH-20 column, with ratio of diameter to height of column being 1:5 and sample injection volume being 10% of bed volume, at an elution flow rate of 5 ml per minute. And the part containing calcium hydroxysafflor yellow A is collected. The solution collected is concentrated at 60° C. and reduced pressure to yield a concentrated solution of refined product of calcium hydroxysafflor yellow A. When calculated as safflower, each kilogram of safflower could yield 35-50 ml of concentrated solution. It is subsequently lyophilized to yield an amber powder of refined product of calcium hydroxysafflor yellow A. The purity is 98.6%. As calculated as safflower, the yield is around 0.50%.

Embodiment 7

Calcium Hydroxysafflor Yellow A (Compound of Formula IV of the Present Invention)

Weigh certain amount of safflower, add deionized water that is 12.5 times of weight of crude drug, extract under a temperature of 100° C. for 20-25 minutes, and filter. Add deionized water that is 10 times of weight of crude drug into the resid, repeat extraction under conditions described above, and filter. Pool the extract from the two steps above, and allow it to cool to ambient temperature. After centrifuging with centrifuge, the centrifugate is taken for further use. The centrifugate above is slowly added into macroporous adsorptive resin separation column, with ratio of diameter to height of column being 1:12 and a sample injection flow of 10 ml per minute. When sample injection is completed, elute with deionized water under room temperature at a flow rate of 20 ml per minute. The eluent is concentrated at 60° C. and reduced pressure to yield a concentrated solution of crude hydroxysafflor yellow. When calculated as safflower, each kilogram of safflower could yield 100 ml of concentrated solution. The concentrated solution of hydroxysafflor yellow undergoes gel LH-20 column, with ratio of diameter to height of column being 1:5 and sample injection volume being 10% of bed volume, using purified water as the eluent, at an elution flow rate of 5 ml per minute. And the part containing hydroxysafflor yellow is collected. The solution collected is concentrated at 60° C. and reduced pressure to yield a concentrated solution of hydroxysafflor yellow. When calculated as safflower, each kilogram of safflower could yield 35-50 ml of concentrated solution. It is subsequently lyophilized to yield an amber powder of hydroxysafflor yellow. The purity is about 90%. The hydroxysafflor yellow powder is dissolved with water, and then acidified with HCl. It is allowed to stand for 2-24 hours in a cool place, until a solid of hydroxysafflor yellow A is formed. Solid is separated and then dissolved with water. Add half the moles of calcium hydroxide as calculated as hydroxysafflor yellow A. It is subsequently lyophilized to yield an amber powder of refined product of calcium hydroxysafflor yellow A. The purity is 99.2%. As calculated as safflower, the yield is around 0.7%.

Embodiment 8

Magnesium Hydroxysafflor Yellow A of Formula III (Compound of Formula V of the Present Invention)

Weigh certain amount of safflower, add deionized water that is 12.5 times of weight of crude drug, extract under a temperature of 100° C. for 20-25 minutes, and filter. Add deionized water that is 10 times of weight of crude drug into the resid, repeat extraction under conditions described above, and filter. Pool the extract from the two steps above, and allow it to cool to ambient temperature. After centrifuging with centrifuge, the centrifugate is taken for further use. The centrifugate above is added into preconditioned 001*7 strongly acidic H-type cation exchange resin, with ratio of diameter to height of column being 1:10 and column volume being 500 ml, under a flow rate of 3 ml/min. The effluent is collected. Add half the moles of magnesium hydroxide as calculated as hydroxysafflor yellow A. Then the resulting solution is slowly added into macroporous adsorptive resin separation column, with ratio of diameter to height of column being 1:12 and a sample injection flow of 10 ml per minute. When sample injection is completed, elute with deionized water under room temperature at a flow rate of 20 ml per minute. The eluent is concentrated at 60° C. and reduced pressure to yield a concentrated solution of crude magnesium hydroxysafflor yellow A. When calculated as safflower, each kilogram of safflower could yield 100 ml of concentrated solution. The concentrated solution of magnesium hydroxysafflor yellow A undergoes gel LH-20 column, with ratio of diameter to height of column being 1:5 and sample injection volume being 10% of bed volume, at an elution flow rate of 5 ml per minute. And the part containing magnesium hydroxysafflor yellow A is collected. The solution collected is concentrated at 60° C. and reduced pressure to yield a concentrated solution of refined product of magnesium hydroxysafflor yellow A. When calculated as safflower, each kilogram of safflower could yield 35-50 ml of concentrated solution. It is subsequently lyophilized to yield an amber powder of refined product of magnesium hydroxysafflor yellow A. The purity is 99.0%. As calculated as safflower, the yield is around 0.5%.

MS, ¹H-NMR, ¹³C-NMR data of magnesium hydroxysafflor yellow A are as following:

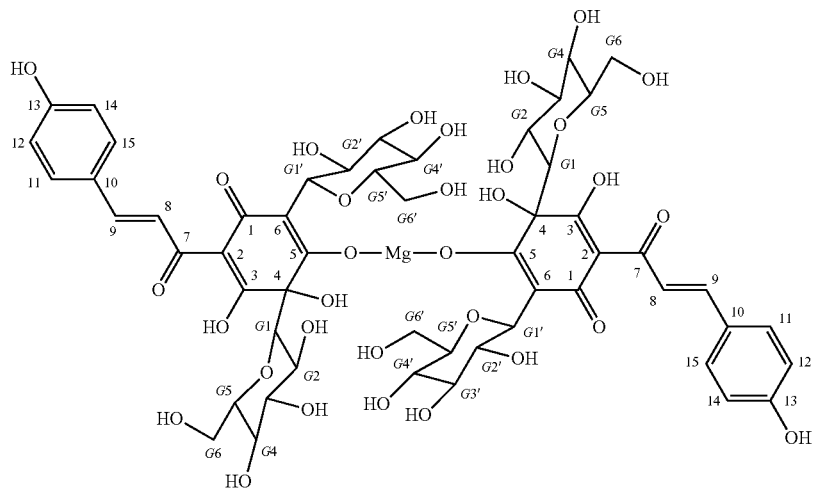

Figure 3:
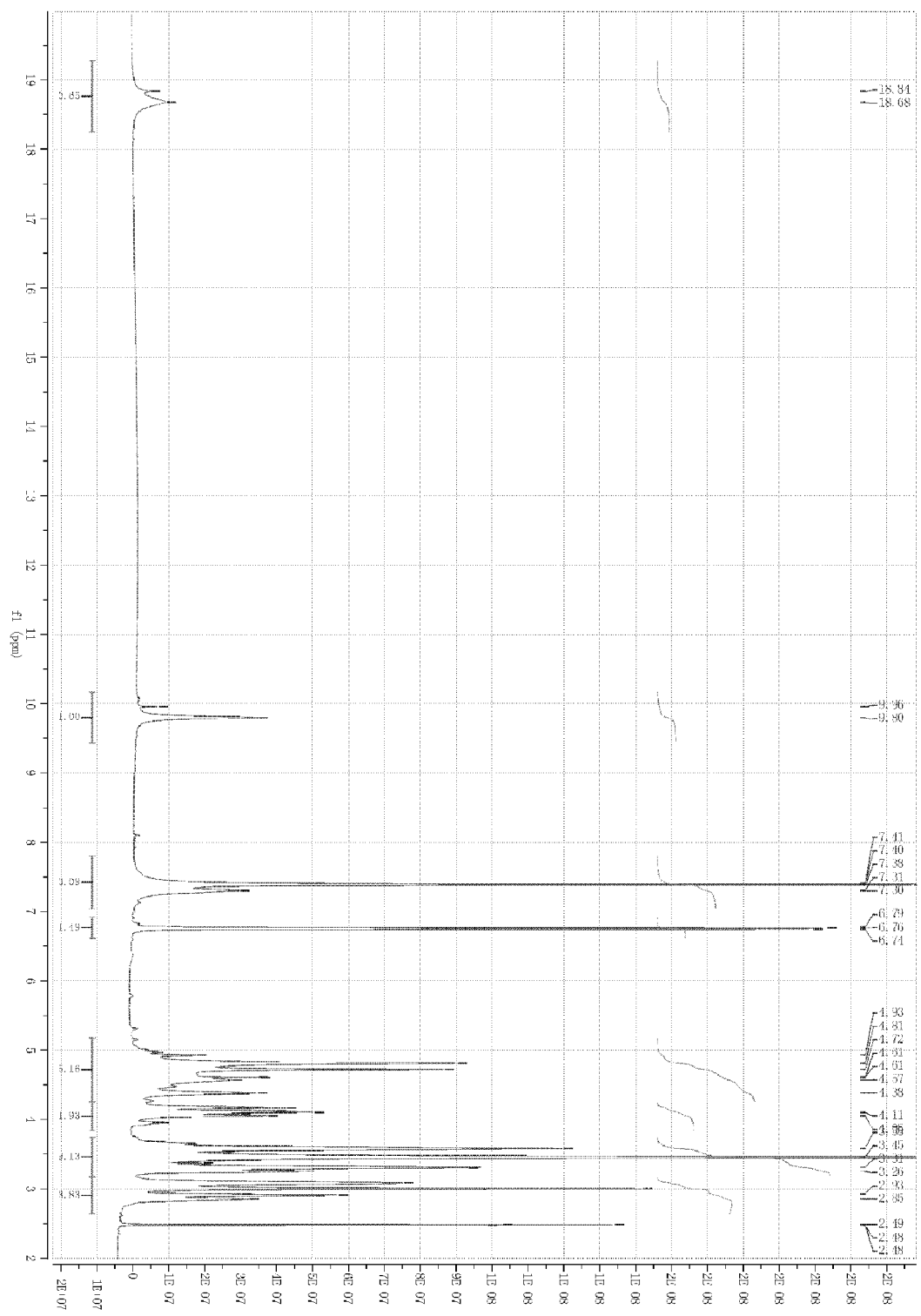
FIG. 3: $^1$H-NMR of magnesium hydroxysafflor yellow A of formula (V)
Figure 4:
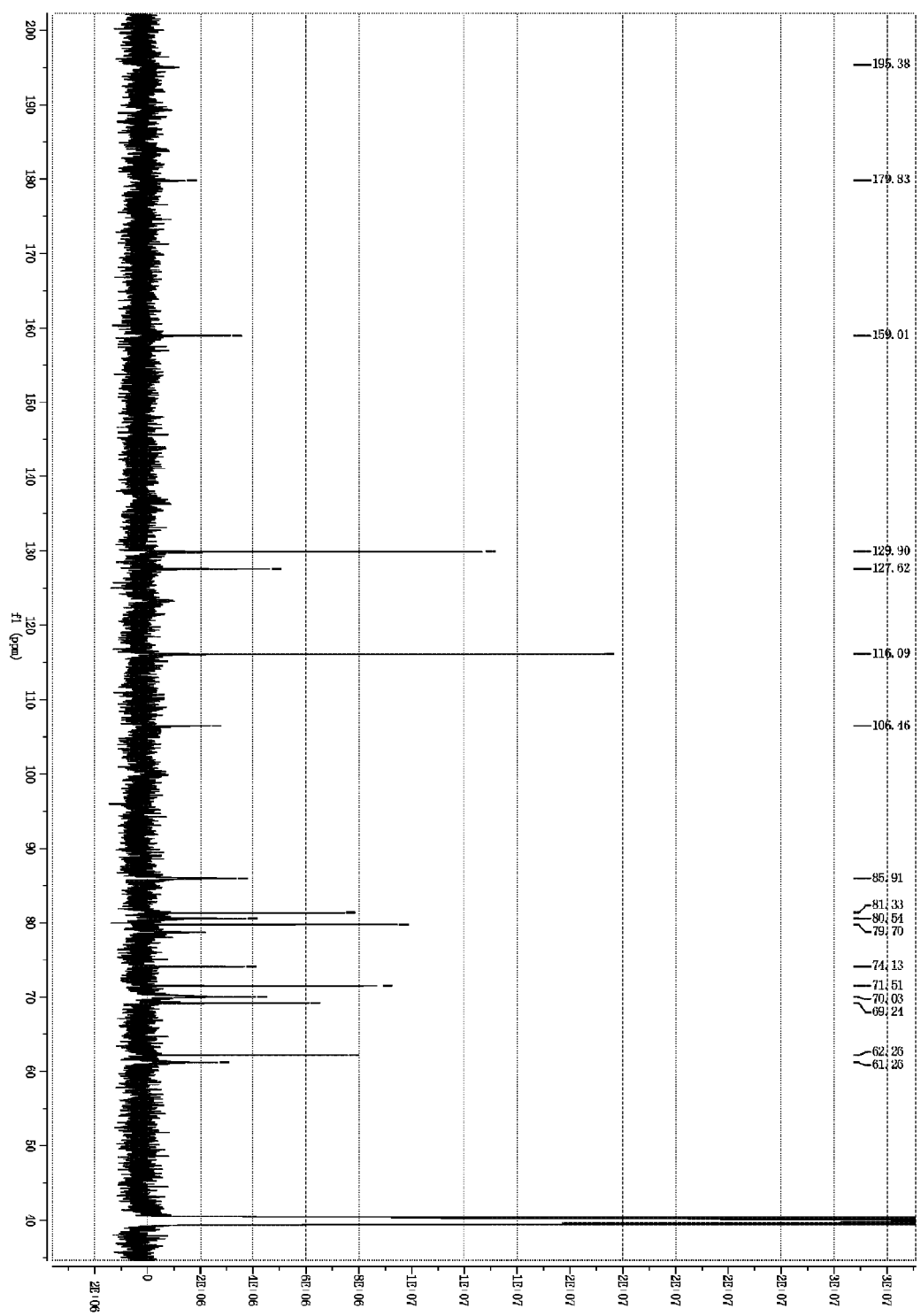
FIG. 4: $^{13}$C-NMR of magnesium hydroxysafflor yellow A of formula (V)

1. MS
Instrument model: LCQ-DECAXP (FINNIGAN Corporation, USA)
Testing condition: ESI
MS
+c ESI 1247.01 (M)⁺
−c ESI 611.35 (M-H)⁻
2. ¹H-NMR and ¹³C-NMR
Instrument model: BRUCKER AVANCE III Model 500 superconducting nuclear magnetic resonance analyser
Testing condition: solvent: DMSO, internal standard: TMS
See FIGS. 3 and 4 for results.
¹H-NM and ¹³C-NMR of magnesium hydroxysafflor yellow A is similar to cases (sodium esomeprazole and magnesium esomeprazole), since presence of magnesium may interfere testing of sample. Only part of ¹H-NMR and ¹³C-NMR could be obtained. Since both process and skeleton structure are consistent with calcium hydroxysafflor yellow A, it may be used as the reference.
¹H-NMR Data Attribution of Magnesium Hydroxysafflor Yellow A (Due to Symmetrical Structure, the Numbers are Consistent)
Chemical shift δ(ppm) 2.85-4.11 is attributed to hydrogen of saccharide part, G1-G6 and G'1-G'6; 4.38-4.81 is attributed to hydroxyl hydrogen on saccharide; 7.30 (1H), 7.38 (1H) are attributed to 8 and 9; 6.74-7.41 (4H) is attributed to 11-15; 18.68 (1H) is attributed to 3-OH; 4.72 (1H) is attributed to 4-OH; and 9.80 (1H) is attributed to 13-OH.
¹³C-NMR Data Attribution of Magnesium Hydroxysafflor Yellow A
Chemical shift δ(ppm) 61.26 (1C), 62.26 (1C) (secondary carbon) are attributed to carbon of saccharide part G6, G'6; 69.24, 70.03, 71.51, 74.13, 79.70, 80.54, 81.33, 85.91 (8C) (tertiary carbon) are attributed to carbon of saccharide part, G1-G5 and G'1-G'5 part; 116.09 (2C) (tertiary carbon) is attributed to 12 and 14; 129.90 (2C) (tertiary carbon) is attributed to 11 and 15; 122.81 (1C), 136.56 (1C) (tertiary carbon) are attributed to 8 and 9;
Chemical shift δ(ppm) 195.38 (1C) is attributed to 3; 179.83 (1C), 127.62 (1C), 159.01 (1C) are attributed to 7, 10, 13, respectively.

Embodiment 9

Magnesium Hydroxysafflor Yellow A (Compound of Formula V of the Present Invention)

Weigh certain amount of safflower, add deionized water that is 12.5 times of weight of crude drug, extract under a temperature of 100° C. for 20-25 minutes, and filter. Add deionized water that is 10 times of weight of crude drug into the resid, repeat extraction under conditions described above, and filter. Pool the extract from the two steps above, and allow it to cool to ambient temperature. After centrifuging with centrifuge, the centrifugate is taken for further use. The centrifugate above is slowly added into macroporous adsorptive resin separation column, with ratio of diameter to height of column being 1:12 and a sample injection flow of 10 ml per minute. When sample injection is completed, elute with deionized water under room temperature at a flow rate of 20 ml per minute. The eluent is concentrated at 60° C. and reduced pressure to yield a concentrated solution of crude hydroxysafflor yellow. When calculated as safflower, each kilogram of safflower could yield 100 ml of concentrated solution. The concentrated solution of hydroxysafflor yellow undergoes gel LH-20 column, with ratio of diameter to height of column being 1:5 and sample injection volume being 10% of bed volume, using purified water as the eluent, at an elution flow rate of 5 ml per minute. And the part containing hydroxysafflor yellow is collected. The solution collected is concentrated at 60° C. and reduced pressure to yield a concentrated solution of hydroxysafflor yellow. When calculated as safflower, each kilogram of safflower could yield 35-50 ml of concentrated solution. It is subsequently lyophilized to yield an amber powder of hydroxysafflor yellow. The purity is about 90%. The hydroxysafflor yellow powder is dissolved with water, and then acidified with HCl. It is allowed to stand for 2-24 hours in a cool place, until a solid of hydroxysafflor yellow A is formed. Solid is separated and then dissolved with water. Add half the moles of magnesium hydroxide as calculated as hydroxysafflor yellow A. It is subsequently lyophilized to yield an amber powder of refined product of magnesium hydroxysafflor yellow A. The purity is 99.2%. As calculated as safflower, the yield is around 0.7%.

Embodiment 10

Triethylamine Hydroxysafflor Yellow A (i.e., in Formula I, n=1, R1=Hydrogen, R2, R3, R4=Ethyl Group)

Weigh certain amount of safflower, add deionized water that is 12.5 times of weight of crude drug, extract under a temperature of 100° C. for 20-25 minutes, and filter. Add deionized water that is 10 times of weight of crude drug into the resid, repeat extraction under conditions described above, and filter. Pool the extract from the two steps above, and allow it to cool to ambient temperature. After centrifuging with centrifuge, the centrifugate is taken for further use. The centrifugate above is added into preconditioned 001*7 strongly acidic H-type cation exchange resin, with ratio of diameter to height of column being 1:10 and column volume being 500 ml, under a flow rate of 3 ml/min. The effluent is collected. Add the same moles of triethylamine as calculated as hydroxysafflor yellow A. Then the resulting solution is slowly added into macroporous adsorptive resin separation column, with ratio of diameter to height of column being 1:12 and a sample injection flow of 10 ml per minute. When sample injection is completed, elute with deionized water under room temperature at a flow rate of 20 ml per minute. The eluent is concentrated at 60° C. and reduced pressure to yield a concentrated solution of crude triethylamine hydroxysafflor yellow A. When calculated as safflower, each kilogram of safflower could yield 100 ml of concentrated solution. The concentrated solution of triethylamine hydroxysafflor yellow A undergoes gel LH-20 column, with ratio of diameter to height of column being 1:5 and sample injection volume being 10% of bed volume, at an elution flow rate of 5 ml per minute. And the part containing triethylamine hydroxysafflor yellow A is collected. The solution collected is concentrated at 60° C. and reduced pressure to yield a concentrated solution of refined product of triethylamine hydroxysafflor yellow A. When calculated as safflower, each kilogram of safflower could yield 35-50 ml of concentrated solution. It is subsequently lyophilized to yield an amber powder of refined product of triethylamine hydroxysafflor yellow A. The purity is 99.0%. As calculated as safflower, the yield is around 0.45%.

Embodiment 11

Triethylamine Hydroxysafflor Yellow A (i.e., in Formula I, n=1, R1=Hydrogen, R2, R3, R4=Ethyl Group)

Weigh certain amount of safflower, add deionized water that is 12.5 times of weight of crude drug, extract under a temperature of 100° C. for 20-25 minutes, and filter. Add deionized water that is 10 times of weight of crude drug into the resid, repeat extraction under conditions described above, and filter. Pool the extract from the two steps above, and allow it to cool to ambient temperature. After centrifuging with centrifuge, the centrifugate is taken for further use. The centrifugate above is added into preconditioned HB-8 macroporous strongly acidic H-type cation exchange resin, with ratio of diameter to height of column being 1:10 and column volume being 500 ml, under a flow rate of 3 ml/min. The effluent is collected. Add the same moles of triethylamine as calculated as hydroxysafflor yellow A. Then the resulting solution is slowly added into macroporous adsorptive resin separation column, with ratio of diameter to height of column being 1:12 and a sample injection flow of 10 ml per minute. When sample injection is completed, elute with deionized water under room temperature at a flow rate of 20 ml per minute. The eluent is concentrated at 60° C. and reduced pressure to yield a concentrated solution of crude triethylamine hydroxysafflor yellow A. When calculated as safflower, each kilogram of safflower could yield 100 ml of concentrated solution. The concentrated solution of triethylamine hydroxysafflor yellow A undergoes gel LH-20 column, with ratio of diameter to height of column being 1:5 and sample injection volume being 10% of bed volume, at an elution flow rate of 5 ml per minute. And the part containing triethylamine hydroxysafflor yellow A is collected. The solution collected is concentrated at 60° C. and reduced pressure to yield a concentrated solution of refined product of triethylamine hydroxysafflor yellow A. When calculated as safflower, each kilogram of safflower could yield 35-50 ml of concentrated solution. It is subsequently lyophilized to yield an amber powder of refined product of triethylamine hydroxysafflor yellow A. The purity is 99.0%. As calculated as safflower, the yield is around 0.47%.

Embodiment 12

Tetramethylammonium Hydroxysafflor Yellow A (i.e., in Formula I, n=1, R1, R2, R3, R4=Methyl)

Weigh certain amount of safflower, add deionized water that is 12.5 times of weight of crude drug, extract under a temperature of 100° C. for 20-25 minutes, and filter. Add deionized water that is 10 times of weight of crude drug into the resid, repeat extraction under conditions described above, and filter. Pool the extract from the two steps above, and allow it to cool to ambient temperature. After centrifuging with centrifuge, the centrifugate is taken for further use. The centrifugate above is added into preconditioned 001*7 strongly acidic H-type cation exchange resin, with ratio of diameter to height of column being 1:10 and column volume being 500 ml, under a flow rate of 3 ml/min. The effluent is collected. Add the same moles of tetramethylammonium hydroxide as calculated as hydroxysafflor yellow A. Then the resulting solution is slowly added into macroporous adsorptive resin separation column, with ratio of diameter to height of column being 1:12 and a sample injection flow of 10 ml per minute. When sample injection is completed, elute with deionized water under room temperature at a flow rate of 20 ml per minute. The eluent is concentrated at 60° C. and reduced pressure to yield a concentrated solution of crude tetramethylammonium hydroxysafflor yellow A. When calculated as safflower, each kilogram of safflower could yield 100 ml of concentrated solution. The concentrated solution of tetramethylammonium hydroxysafflor yellow A undergoes gel LH-20 column, with ratio of diameter to height of column being 1:5 and sample injection volume being 10% of bed volume, at an elution flow rate of 5 ml per minute. And the part containing tetramethylammonium hydroxysafflor yellow A is collected. The solution collected is concentrated at 60° C. and reduced pressure to yield a concentrated solution of refined product of tetramethylammonium hydroxysafflor yellow A. When calculated as safflower, each kilogram of safflower could yield 35-50 ml of concentrated solution. It is subsequently lyophilized to yield an amber powder of refined product of tetramethylammonium hydroxysafflor yellow A. The purity is 99.0%. As calculated as safflower, the yield is around 0.45%.

MS, $^1$H-NMR data of Tetramethylammonium hydroxysafflor yellow A are as following:

1. MS

Instrument model: LCQ-DECAXP (FINNIGAN Corporation, USA)

Testing condition: ESI

MS

−c ESI 611.22 (M-H)$^−$

2. $^1$H-NMR

Instrument model: BRUCKER AVANCE III Model 500 superconducting nuclear magnetic resonance analyser Testing condition: solvent: DMSO, internal standard: TMS $^1$H-NMR Data of Tetramethylammonium Hydroxysafflor Yellow A

|  | Chemical shift δ (ppm) | Proton number |
|---|---|---|
| Proton order (H attribution) |  |  |
| 8 | 7.25 | 1 |
| 9 | 7.39 | 1 |
| 11, 15 | 7.41 | 2 |
| 12, 14 | 6.76 | 2 |
| 3-OH | 18.66 | 1 |
| 4-OH | 4.73 | 1 |
| 5-ON(CH$_3$)$_4$ | 6.90-7.33 | 12 |
| 13-OH | 9.74 | 1 |
| Saccharide part |  |  |
| G1 | 3.60 | 1 |
| G2 | 2.82 | 1 |
| G3 | 3.06 | 1 |
| G4 | 3.27 | 1 |
| G5 | 3.01 | 1 |
| G6 | 3.36-3.22 | 2 |

-continued

|  | Chemical shift δ (ppm) | Proton number |
|---|---|---|
| G'1 | 4.15 | 1 |
| G'2 | 4.03 | 1 |
| G'3 | 3.07 | 1 |
| G'4 | 3.04 | 1 |
| G'5 | 2.91 | 1 |
| G'6 | 3.59 | 2 |
| Hydroxyl on saccharide | 4.40~4.78 | 8 |

What is claimed is:

1. A pharmaceutically acceptable salt of hydroxysafflor yellow A of a formula (I),

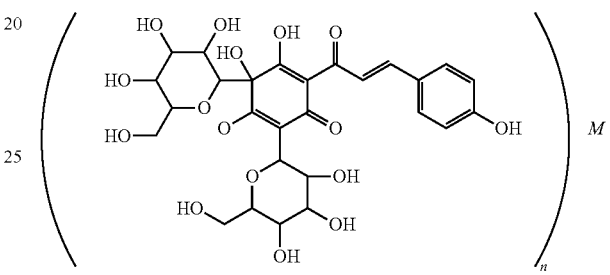

Formula (I)

wherein n is 1 or 2, and M is chosen from Ca, Mg, K, NH$_4$ or

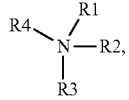

wherein R1, R2, R3 and R4 are identical or different, and chosen from a hydrogen or an alkyl group independently.

2. The pharmaceutically acceptable salt of the hydroxysafflor yellow A of claim 1, characterized in that the pharmaceutically acceptable salt of the hydroxysafflor yellow A is chosen from a potassium salt of a formula (II), an ammonium salt of a formula (III), a calcium salt of a formula (IV), or a magnesium salt of a formula (V):

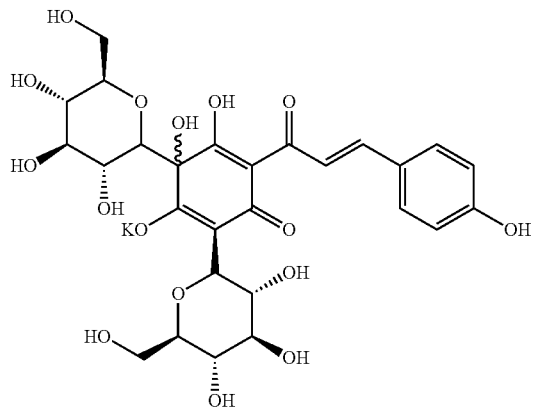

Formula (II)

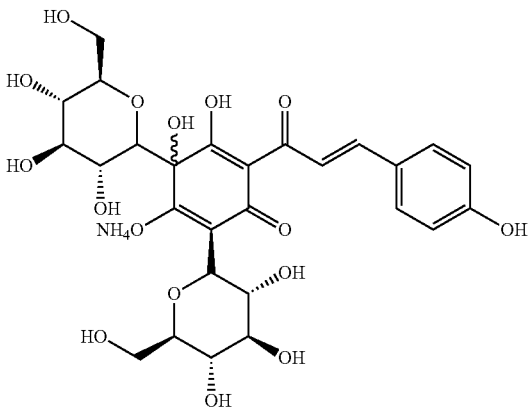

Formula (III)

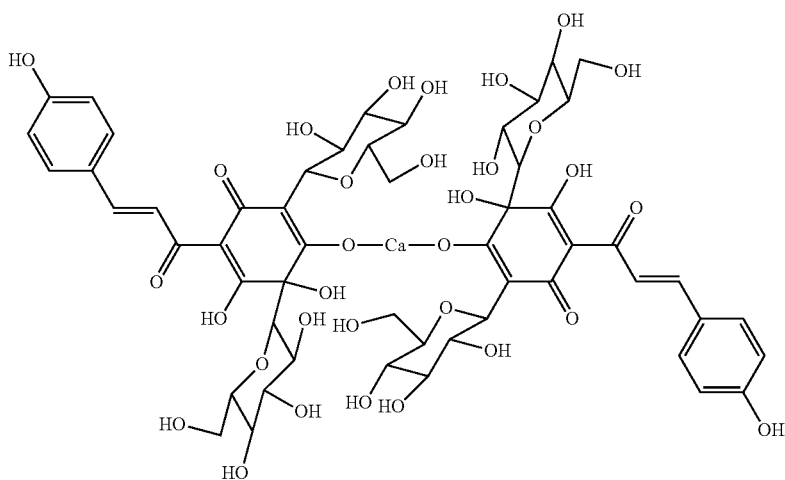

Formula (IV)

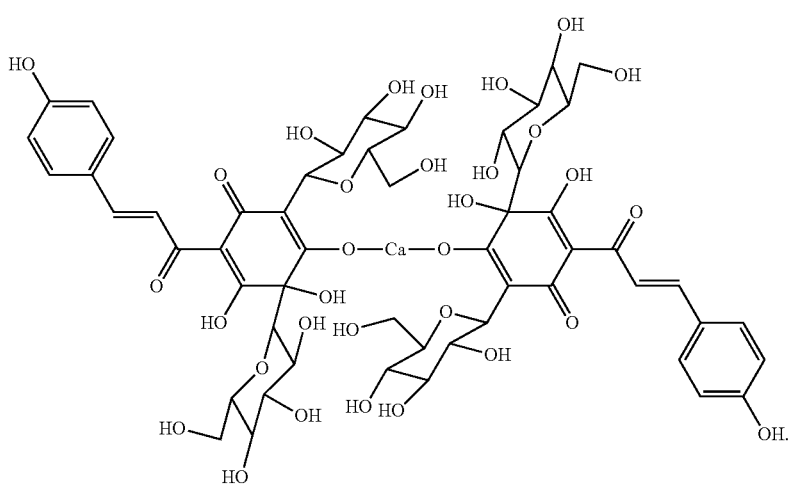

Formula (V)

3. A method for preparing pharmaceutically acceptable salt of hydroxysafflor yellow A, including steps of: extracting from saffron herbs, converting with strongly acidic H-type cation exchange resin, macroporous adsorptive resin separating, processing with dextran gel chromatography and ultrafiltrating, characterized by:

(1) extracting from saffron herbs: using saffron herbs as a raw material, wherein an extract containing hydroxysafflor yellow A is obtained through water extraction;

(2) converting with strongly acidic H-type cation exchange resin: passing the extract obtained in the Step (1) through a strongly acidic H-type cation exchange resin column, collecting eluent, adding potassium hydroxide, ammonium hydroxide, alkylamine or alkyl ammonium, magnesium hydroxide, calcium hydroxide, magnesium carbonate or calcium carbonate, to convert the hydroxysafflor yellow A into the pharmaceutically acceptable salt of the hydroxysafflor yellow A, and then collecting eluent containing the pharmaceutically acceptable salt of the hydroxysafflor yellow A;

(3) macroporous adsorptive resin separating: separating the eluent containing the pharmaceutically acceptable salt of the hydroxysafflor yellow A prepared in the Step (2) with a macroporous adsorptive resin column, using water as eluent; collecting the eluent and concentrating under a reduced pressure, to yield a crude pharmaceutically acceptable salt of the hydroxysafflor yellow A;

(4) processing with dextran gel chromatography: undergoing the crude pharmaceutically acceptable salt of the hydroxysafflor yellow A obtained in the Step (3) with dextran gel chromatographic separation, using water as eluent, collecting the eluent containing the pharmaceutically acceptable salt of the hydroxysafflor yellow A; and (5) ultrafiltrating: concentrating the eluent containing the pharmaceutically acceptable salt of the hydroxysafflor yellow A obtained from the Step (4), and then filtering or centrifuging; ultrafiltrating by using an ultrafiltration membrane with molecular weight cutoff (MWCO) of 8000-10000 Daltons to obtain ultrafiltrate, which is subsequently dried to yield the pharmaceutically acceptable salt of the hydroxysafflor yellow A;

or the method includes steps of extracting from saffron herbs, macroporous adsorptive resin separating, processing with dextran gel chromatography, ultrafiltrating, acidifying and salifying, characterized by:

(1) extracting from saffron herbs: using saffron herbs as a raw material, wherein an extract containing hydroxysafflor yellow A is obtained through water extraction;

(2) macroporous adsorptive resin separating: separating the extract containing the hydroxysafflor yellow prepared in the Step (1) with a macroporous adsorptive resin column, using water as eluent; collecting the eluent and concentrating under a reduced pressure, to yield a crude hydroxysafflor yellow;

(3) processing with dextran gel chromatography: undergoing the crude hydroxysafflor yellow prepared in the Step (2) with dextran gel chromatographic separation, using water as eluent; collecting the eluent containing the hydroxysafflor yellow;

(4) ultrafiltrating: concentrating the eluent containing the hydroxysafflor yellow A obtained from the Step (3), and then filtering or centrifuging; ultrafiltrating by using an ultrafiltration membrane with MWCO of 8000-10000 Daltons to obtain ultrafiltrate, which is subsequently dried to yield the hydroxysafflor yellow powder;

(5) acidifying: adding water and then acid into the hydroxysafflor yellow powder obtained from the Step (4); allowing to stand for 2-24 hours in a cool place, until an amber solid of hydroxysafflor yellow A is formed; then removing the supernatant liquid through filtering; and (6) salifying: adding water, and then potassium hydroxide, ammonium hydroxide, alkylamine or alkyl ammonium, magnesium hydroxide, calcium hydroxide, magnesium carbonate or calcium carbonate, into the hydroxysafflor yellow A obtained in the Step (5) to convert the hydroxysafflor yellow A into the pharmaceutically acceptable salt of the hydroxysafflor yellow A; wherein again ultrafiltration is carried out with an ultrafiltration membrane; and the pharmaceutically acceptable salt of the hydroxysafflor yellow A is obtained through lyophilisation.

4. The method of claim 3, wherein the cation exchange resin described in the Step (2) is the strongly acidic H-type cation exchange resin, which is chosen from 001*7 ion exchange resin or macroporous HB-8 exchange resin.

5. A pharmaceutical composition comprising therapeutic amount of pharmaceutically acceptable salt of hydroxysafflor yellow A as an active ingredient, and pharmaceutically acceptable carrier as an adjuvant.

6. The pharmaceutical composition of claim 5, wherein the pharmaceutical composition is a lyophilized powder for injection or infusion.

7. The pharmaceutical composition of claim 6, wherein the pharmaceutical composition is a lyophilized powder for injection, and prepared through a process including the following steps of:

(1) using saffron herbs as a raw material, adding water at 50-100° C. for extraction, which is carried out by extracting with water for 2-3 times, 0.5-24 hours each time; wherein an amount of the water used for extraction is 10-30 times of crude safflower; after extraction, gruffs is filtered out; the extract is cooled to 5-30° C. and allowed to stand for 2-24 hours;

(2) flowing the extract prepared in the Step (1) through strongly acidic H-type cation exchange resin at a rate of 1-30 ml/min; adding potassium hydroxide, ammonium hydroxide, alkylamine or alkyl ammonium, magnesium hydroxide, calcium hydroxide, magnesium carbonate or calcium carbonate, to convert the hydroxysafflor yellow A into the pharmaceutically acceptable salt of the hydroxysafflor yellow A; collecting eluent containing the pharmaceutically acceptable salt of the hydroxysafflor yellow A;

(3) undergoing the eluent prepared in the Step (2) with macroporous adsorptive resin column separation, using purified water as eluent and at an elution flow rate of 10-30 ml/min; collecting the eluent, and concentrating at a reduced pressure, to yield a concentrated solution of a crude pharmaceutically acceptable salt of the hydroxysafflor yellow A;

(4) after filtering or centrifuging the concentrated solution of the crude pharmaceutically acceptable salt of the hydroxysafflor yellow A obtained in the Step (3), providing dextran gel chromatographic separation, using purified water as eluent, and at a controlled linear elution flow rate of 1-10 cm/h; collecting the eluent containing the pharmaceutically acceptable salt of the hydroxysafflor yellow A, and concentrating at the reduced pressure, to yield a concentrated solution;

(5) after filtering or centrifuging the concentrated solution obtained from the Step (4), ultrafiltrating with an ultrafiltration membrane of MWCO 8000-10000 Daltons, to yield ultrafiltrate;

(6) lyophilizing the ultrafiltrate obtained from the Step (5) to yield a refined product of the pharmaceutically acceptable salt of the hydroxysafflor yellow A; and (7) dissolving the refined product of the pharmaceutically acceptable salt of the hydroxysafflor yellow A obtained from the Step (6) in water for injection; wherein resulting solution is filtered through a micropore film of 0.22 μm or the ultrafiltration membrane of MWCO 8000-10000 Daltons, and then transferred into bottles as aliquots; the resulting solution is subsequently lyophilized to yield lyophilized powder for injection of the pharmaceutically acceptable salt of the hydroxysafflor yellow A;

wherein:

the strongly acidic H-type cation exchange resin is 001*7 ion exchange resin or macroporous HB-8 exchange resin;

the macroporous adsorptive resin is macroporous adsorptive resin HZ801;

the dextran gel chromatography uses dextran gel LH-20.

8. A method for preparing a medicine, comprising: applying a pharmaceutically acceptable salt of hydroxysafflor yellow A, or pharmaceutical composition thereof, wherein the medicine has efficacy against platelet aggregation induced by PAF or ADP, or the medicine is intended to be used for treating or preventing diseases involving injury due to myocardial ischemia, cerebral ischemia or thrombosis.

* * * * *